(12) United States Patent
Parish et al.

(10) Patent No.: US 8,327,973 B2
(45) Date of Patent: Dec. 11, 2012

(54) FOAM COMPOSITIONS WITH ENHANCED SOUND ATTENUATION

(75) Inventors: William Parish, Maplewood, MN (US); Vasant V. Kolpe, Mendota Heights, MN (US)

(73) Assignee: Hearing Components, Inc., Oakdale, MN (US)

( * ) Notice: Subject to any disclaimer, the term of this patent is extended or adjusted under 35 U.S.C. 154(b) by 105 days.

(21) Appl. No.: 12/850,491

(22) Filed: Aug. 4, 2010

(65) Prior Publication Data

US 2011/0031059 A1    Feb. 10, 2011

Related U.S. Application Data

(60) Provisional application No. 61/231,259, filed on Aug. 4, 2009.

(51) Int. Cl.
*A61B 7/02* (2006.01)
*A61F 11/00* (2006.01)
*H04R 25/00* (2006.01)
*H04R 25/02* (2006.01)
*H04R 31/00* (2006.01)

(52) U.S. Cl. .......... 181/129; 29/594; 128/864; 181/130; 181/135; 381/328

(58) Field of Classification Search .............. 181/129, 181/130; 128/864; 381/328; 29/594
See application file for complete search history.

(56) References Cited

U.S. PATENT DOCUMENTS

| | | | |
|---|---|---|---|
| 3,459,274 A | 8/1969 | MacPhail | |
| 3,510,392 A | 5/1970 | Eustachio | |
| 3,747,769 A * | 7/1973 | Brumfield | 210/350 |
| 3,811,437 A * | 5/1974 | Gardner, Jr. | 128/864 |
| 3,993,608 A | 11/1976 | Wells | |
| 4,013,810 A | 3/1977 | Long | |
| 4,079,162 A | 3/1978 | Metzger | |
| 4,176,218 A * | 11/1979 | Demou et al. | 521/129 |
| 4,434,794 A * | 3/1984 | Leight | 128/867 |
| 4,465,159 A | 8/1984 | Stallings | |
| 4,660,412 A | 4/1987 | Gupta | |
| 4,774,938 A * | 10/1988 | Leight | 128/864 |
| 4,788,225 A * | 11/1988 | Edwards et al. | 521/147 |
| 4,880,076 A * | 11/1989 | Ahlberg et al. | 181/130 |
| 5,002,151 A * | 3/1991 | Oliveira et al. | 181/130 |

(Continued)

FOREIGN PATENT DOCUMENTS

EP    1192920 A1 *  4/2002

(Continued)

OTHER PUBLICATIONS

Krupers, Maarten J. et al., "Formation of rigid polyurethane foams with semi-fluorinated diblock copolymeric surfacants," 39(10): 2049-2053, 1998.

(Continued)

*Primary Examiner* — David Warren
*Assistant Examiner* — Christina Russell
(74) *Attorney, Agent, or Firm* — Seager Tufte & Wickhem LLC

(57) ABSTRACT

Disclosed are foam compositions with enhanced sound attenuation characteristics for use in earpieces, for example, user-disposable foam members such as foam tips for sound control devices including sound transmission devices and earplugs in which a relationship between the size of the pores and the volume of the cells of the polymeric may be controlled.

35 Claims, 11 Drawing Sheets

U.S. PATENT DOCUMENTS

| | | | |
|---|---|---|---|
| 5,068,902 A | 11/1991 | Ward | |
| 5,203,352 A * | 4/1993 | Gardner, Jr. | 128/864 |
| 5,401,920 A | 3/1995 | Oliveira | |
| 5,422,380 A * | 6/1995 | Mendelsohn et al. | 521/107 |
| 5,477,255 A * | 12/1995 | Huth | 347/87 |
| 5,603,340 A * | 2/1997 | Gueret | 132/293 |
| 5,622,662 A | 4/1997 | Veiga | |
| 5,658,656 A | 8/1997 | Whitney et al. | |
| 5,682,020 A * | 10/1997 | Oliveira | 181/130 |
| 5,773,121 A | 6/1998 | Meteer et al. | |
| 5,792,998 A * | 8/1998 | Gardner et al. | 181/130 |
| 5,799,658 A * | 9/1998 | Falco | 128/864 |
| 5,917,918 A * | 6/1999 | Callahan | 381/67 |
| 5,920,636 A | 7/1999 | Oliveira et al. | |
| 5,979,451 A * | 11/1999 | Leight | 128/864 |
| 5,996,584 A | 12/1999 | Oliveira | |
| 6,006,857 A * | 12/1999 | Leight et al. | 181/135 |
| 6,080,800 A * | 6/2000 | Frey et al. | 521/132 |
| 6,310,961 B1 * | 10/2001 | Oliveira et al. | 381/328 |
| 6,408,981 B1 * | 6/2002 | Smith et al. | 181/126 |
| 6,481,490 B1 * | 11/2002 | Vihtelic et al. | 164/516 |
| 6,541,105 B1 * | 4/2003 | Park | 428/304.4 |
| 6,720,362 B1 * | 4/2004 | Park | 521/79 |
| 6,789,646 B2 | 9/2004 | Wang et al. | |
| 7,236,605 B2 * | 6/2007 | Oliveira et al. | 381/328 |
| 7,263,028 B2 | 8/2007 | Thomas et al. | |
| 7,313,245 B1 * | 12/2007 | Shennib | 381/325 |
| 7,349,550 B2 | 3/2008 | Oliveira et al. | |
| 7,600,604 B2 * | 10/2009 | Babcock et al. | 181/130 |
| 2005/0038160 A1 | 2/2005 | Hall et al. | |
| 2005/0042437 A1 | 2/2005 | Ramesh | |
| 2006/0175722 A1 * | 8/2006 | Babcock et al. | 264/41 |
| 2007/0036379 A1 | 2/2007 | Anderson et al. | |
| 2007/0125590 A1 * | 6/2007 | Oberdanner | 181/135 |
| 2008/0050576 A1 | 2/2008 | Pierick et al. | |
| 2008/0226114 A1 * | 9/2008 | Thompson et al. | 381/380 |
| 2009/0232342 A1 | 9/2009 | Oliveira et al. | |
| 2009/0270523 A1 * | 10/2009 | Dai et al. | 521/137 |
| 2010/0300461 A1 * | 12/2010 | Gilder et al. | 128/864 |

FOREIGN PATENT DOCUMENTS

WO      9807296 A1      2/1998

OTHER PUBLICATIONS

Seo, W.J. et al., "Mechanical, Morphological, and Thermal Properties of Rigid Polyurethane Foams Blown by Distilled Water," Journal of Applied Science 90: 12-21, 2003.

Brochure, "EXPANCEL microshperes expand—and so does your profitability," Expancel, 2005.

Lee, Sung Ho et al., "Shape memory effects of molded flexible polyurethane foam," Smart Materials and Structures: 2486-2491, 2007.

Chu, Raymond K.M. et al., "Synthesis and Characterization of Open-Cell Foams for Sound Absorption With Rotational Molding Method," Polymer Engineering and Science: 1-11, 2009.

International Search Report and Written Opinion from PCT/US2010/044450, Oct. 4, 2010.

* cited by examiner

US 8,327,973 B2

FOAM COMPOSITIONS WITH ENHANCED SOUND ATTENUATION

CROSS REFERENCE TO RELATED APPLICATIONS

This application claims the benefit of U.S. Provisional Application Ser. No. 61/231,259, filed Aug. 4, 2009, the disclosure of which is incorporated herein by reference.

TECHNICAL FIELD

The disclosure is directed to foam compositions with enhanced sound attenuation. More particularly, the disclosure is directed to foam compositions used in earpiece members of sound control devices for placement in close proximity to an ear canal of a user, such as user-disposable members for placement within the ear canal.

BACKGROUND

User-disposable polymeric foam members for placement within the auditory anatomy, such as the ear canal, of a user are useful to hold in place sound control devices, such as sound transmission and/or attenuation devices, and/or to attenuate unwanted sounds. Similarly, other earpieces for placement over the ear, on the ear, in the ear, or in the ear canal of a user may be used to attenuate sound.

Attenuation of sound energy utilizing viscoelastic polymeric foam may be achieved by various means. Some sound attenuation may be attributed to the mechanical properties of the foam. For instance, the tan delta of the foam is a property of the foam which is used to describe the ability of the polymer to dissipate energy. The tan delta is the ratio of two moduli of the foam called the storage modulus (G') and the loss modulus (G"), thus tan delta=G"/G'. Certain structures produced in the foam can also enhance the sound attenuating capacity of the foam such as a surface skin which acts to reflect some of the sound energy before it enters the foam. Additives to the foam such as fillers of various types can provide reflecting surfaces to also reduce the transmission of sound energy. Another way that foam may attenuate sound energy is by the passage of the sound pressure waves through the pore openings into the individual cells of the foam. Energy is dissipated as the sound energy passes through the pores and enters the individual foam cells.

It is desirable to provide improved foam compositions for user-disposable members, and other earpiece members used as or with sound control devices including sound attenuation devices that have advantageous characteristics such as enhanced sound attenuation.

SUMMARY

The disclosure is directed to several alternative materials, compositions and methods of manufacturing foam with enhanced sound attenuation which may be used in acoustic applications, for example, auditory equipment. In some instances, the foam compositions may be used to form earpieces (e.g., user-disposable foam members), such as foam tips for sound control devices including sound transmission devices and/or earplugs for placement in the ear canal of a user or other earpieces for placement over the ear, on the ear, in the ear, or in the ear canal of a user, or foam sealing layers for over-the-ear type sound control equipment such as headphones, earmuffs or other hearing protection equipment which may provide a sealing layer at the interface between the cups of the earphones or earmuffs and the head of the user surrounding the user's ears, sealing off unwanted sound from entering the user's ear canal and reaching the user's ear drum.

Accordingly, one illustrative embodiment is a sound control device including an earpiece member for placement in close proximity to an ear canal of a user to attenuate sound. The earpiece member includes a polymeric foam material having a plurality of cells defined by interconnected cellular walls of the polymeric foam material and a plurality of pores extending through the cellular walls between adjacent cells to interconnect adjacent cells of the polymeric foam material. The average and/or mode volume of the cells of the polymeric foam material is between about 8,000 microns$^3$ to about 8,000,000 microns$^3$, and the average and/or mode diameter of the pores of the polymeric foam material is between about 5 microns to about 50 microns. The cells of the polymeric foam material may have an average and/or mode diameter between about 25 microns to about 250 microns, and a ratio between the average and/or mode diameter of the pores to the average and/or mode diameter of the cells may be between 0.02 to 0.2.

Another illustrative embodiment is a foam earpiece for a sound control device which can be placed in close proximity of the ear canal of a user to attenuate sound. The foam earpiece includes a polyurethane foam material formed of a polymer mixture of a diisocyanate mixture reacted with a polyol mixture in the presence of a catalyst mixture. The polyurethane foam material has a plurality of open cells defined by interconnected cellular walls of the polyurethane foam material and a plurality of pores extending through the cellular walls between adjacent open cells to interconnect adjacent open cells of the polyurethane foam material. The polyurethane foam material has a percent of open cells of 70% or more. The average volume of the open cells of the polyurethane foam material is between about 8,000 microns$^3$ to about 8,000,000 microns$^3$, and the average diameter of the pores of the polyurethane foam material is between about 5 microns to about 50 microns.

Yet another illustrative embodiment is a method of forming an earpiece member for placement in close proximity to an ear canal of a user for attenuating sound. The method includes reacting a diisocyanate with a polyol mixture in the presence of a catalyst mixture to form a polyurethane foam material having a plurality of cells defined by interconnected cellular walls. The polyurethane foam material is crushed to rupture the cellular walls between adjacent cells of the polyurethane foam material, such that subsequent to crushing the polyurethane foam material, the polyurethane foam material has 80% or more open cells interconnected with adjacent open cells by pores extending through the cellular walls between adjacent open cells. The average volume of the cells of the polyurethane foam material is between about 8,000 microns$^3$ to about 8,000,000 microns$^3$, and the average diameter of the pores of the polyurethane foam material is between about 5 microns to about 50 microns. An earpiece member is formed from the polyurethane foam material.

Another illustrative embodiment is a sound control device including an earpiece member for placement in close proximity to an ear canal of a user for attenuating sound. The earpiece member includes a polymeric foam material having a plurality of cells defined by interconnected cellular walls of the polymeric foam material and a plurality of pores extending through the cellular walls between adjacent cells to interconnect adjacent cells of the polymeric foam material. The polymeric foam material is sufficiently flexible to conform to a contoured portion of a user's anatomy. The average diameter of the pores of the polymeric foam material is between about 5 microns to about 50 microns. In some instances, the polymeric foam material may have a compressional modulus in the range of about 0.5 psi to about 4.5 psi measured at 37 degrees Celsius and 50% relative humidity. In some instances, the cells of the polymeric foam material have an average diameter between about 25 microns to about 250 microns, and a ratio between the average diameter of the pores to the average diameter of the cells is between 0.02 to 0.2.

A further illustrative embodiment is an over-the-ear sound control device including a pair of cups for placement over the ears of a user. Each cup includes a layer of sound attenuating polymeric foam material at an interface between a circumferential rim of the cup and the head of the user. The sound attenuating polymeric foam material is an open cell foam having a plurality of cells defined by interconnected cellular walls of the polymeric foam material and a plurality of pores extending through the cellular walls between adjacent cells to interconnect adjacent cells of the polymeric foam material. The average volume of the cells of the polymeric foam material is between about 8,000 microns$^3$ to about 8,000,000 microns$^3$, and the average diameter of the pores of the polymeric foam material is between about 5 microns to about 50 microns.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
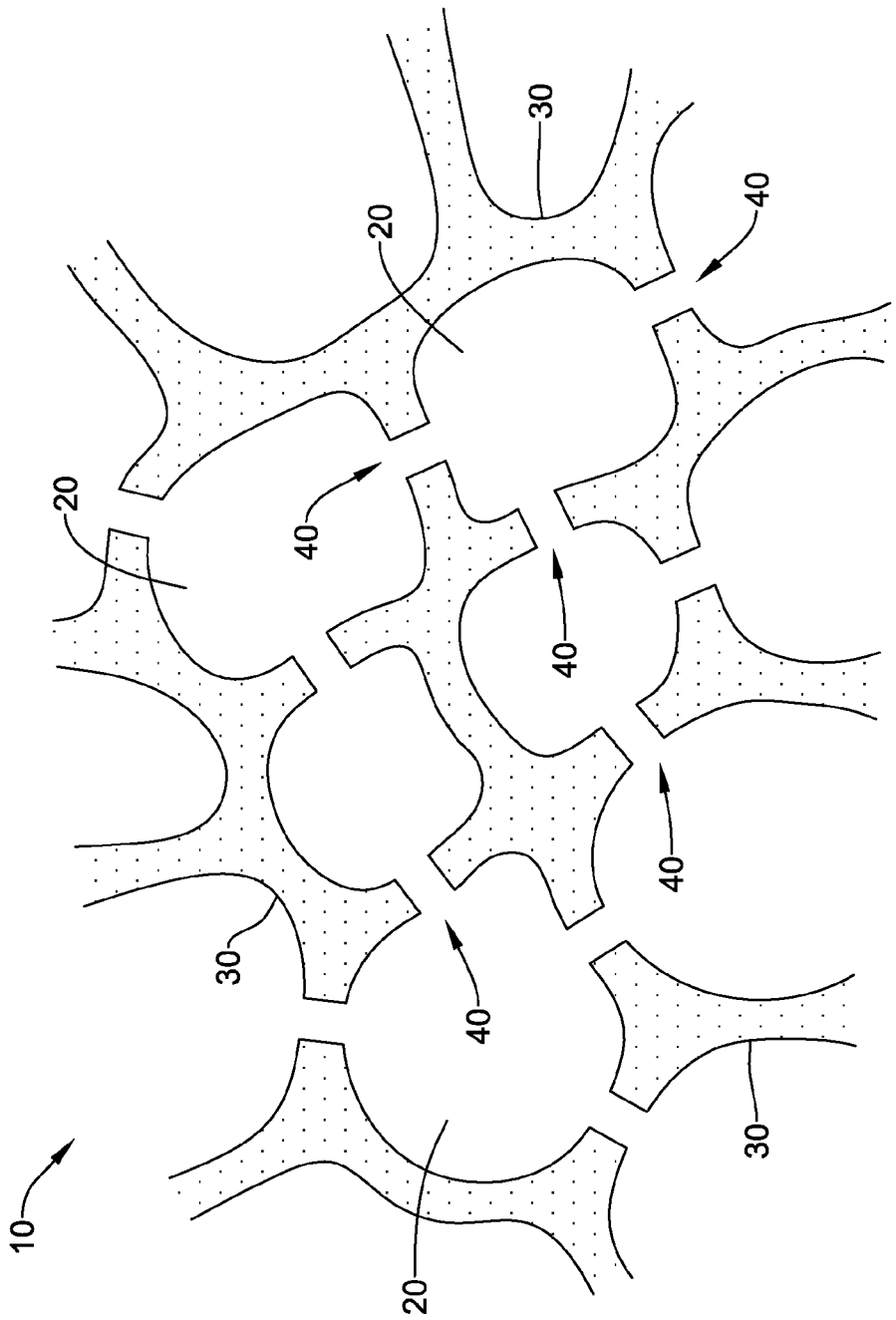
FIG. 1 is a schematic cross-section of a polymeric foam material having a plurality of cells interconnected with a plurality of pores.

While the invention is amenable to various modifications and alternative forms, specifics thereof will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "foam" is intended to mean a polymeric cellular material having numerous cells of gas distributed throughout its mass.

As used in this specification and the appended claims, the term "polyurethane foam" is intended to refer to a family of foam compositions resulting from the introduction of gas bubbles into a polymer matrix made by the reaction of suitable active hydrogen containing compounds with polyisocyanates, and includes foam compositions in which the gas bubbles are introduced simultaneously with the polymer forming reactions.

As used in this specification and the appended claims, the term "cell" is intended to mean a single void defined by cellular walls of a foam material. In instances in which the void is completely surrounded by cellular walls, the cell is said to be closed. In instances in which the void is only partially surrounded by cellular walls (e.g., adjacent cells are interconnected), the cell is said to be open. A completely open cell has no wall membranes but is part of a three dimensional network of connected fibers or rods.

As used in this specification and the appended claims, the term "pore" is intended to mean an opening through a cellular wall which connects one cell to an adjacent cell.

As used in this specification and the appended claims, the term "closed cell foam" is intended to mean a polymeric cellular material having an open cell content of 30 volume percent or less, measured according to ASTM D6226-05.

As used in this specification and the appended claims, the term "open cell foam" is intended to mean a polymeric cellular material having an open cell content of greater than 30 volume percent, measured according to ASTM D6226-05.

As used in the specification and the appended claims, the term "density" is intended to mean the mass per unit volume of a polymeric cellular material.

As used in the specification and the appended claims, the term "slow recovery foam" is intended to mean a polymeric cellular material that exhibits a stress-relaxation phenomenon (i.e., delay of complete deformation recovery after compression) in which the rate of recovery for the polymeric cellular material to recover from 30% compression to 5% compression is from 1 to 60 seconds. As used herein, slow recovery foam is synonymous with viscoelastic foam.

As used in this specification and the appended claims, the term "diisocyanate" is intended to mean any compound containing two isocyanate (—N═C═O) groups, used in the production of polyurethane.

As used in this specification and the appended claims, the term "catalyst" is intended to mean a substance that causes or accelerates a chemical reaction when added to the reactants in a minor amount, and that is not consumed in the reaction.

As used in this specification and the appended claims, the term "polyol" is intended to mean an organic compound having multiple hydroxyl (—OH) groups per molecule. The term includes monomeric and polymeric compounds containing alcoholic hydroxyl groups such as polyethers, glycols, glycerol, and polyesters, used as reactants in polyurethane foam.

As used in this specification and the appended claims, the term "prepolymer" is intended to mean a polymer of relatively low molecular weight, usually intermediate between those of the monomer or monomers and the final polymer or resin, that may be mixed with compounding additives, and that is capable of being further reacted or cured by further polymerization during or after a forming process.

Figure 2:
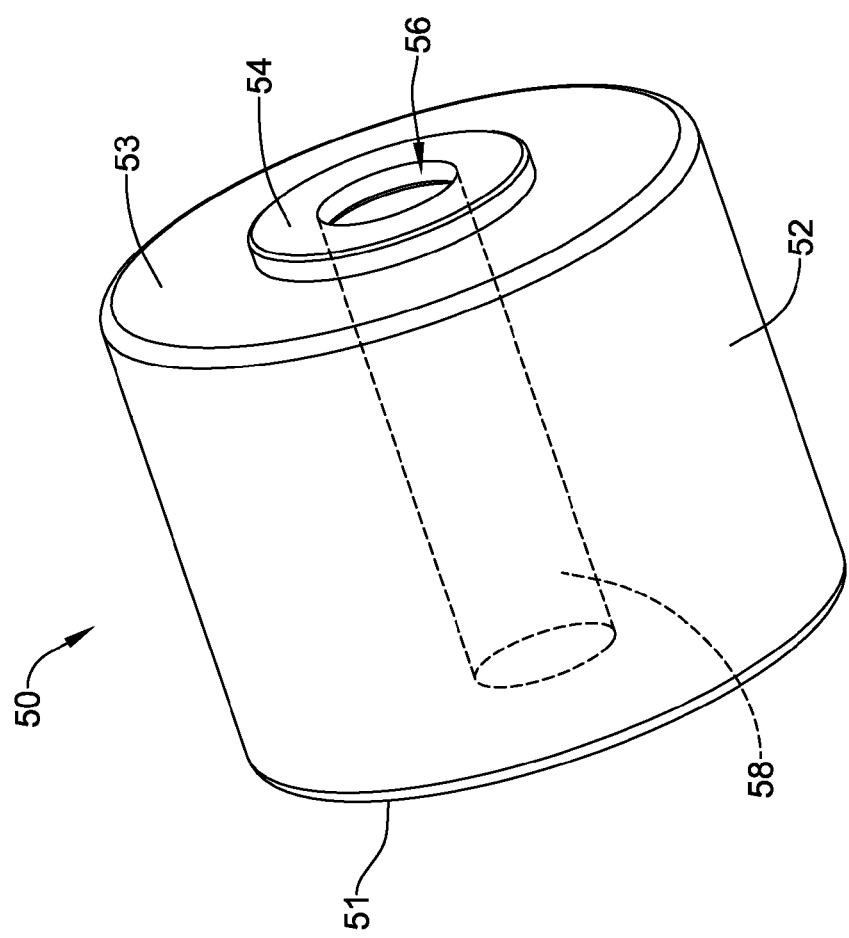
FIG. 2 is a perspective view of a first exemplary earpiece for a sound control device, illustrated as a snap-fit user-disposable foam tip.
Figure 3:
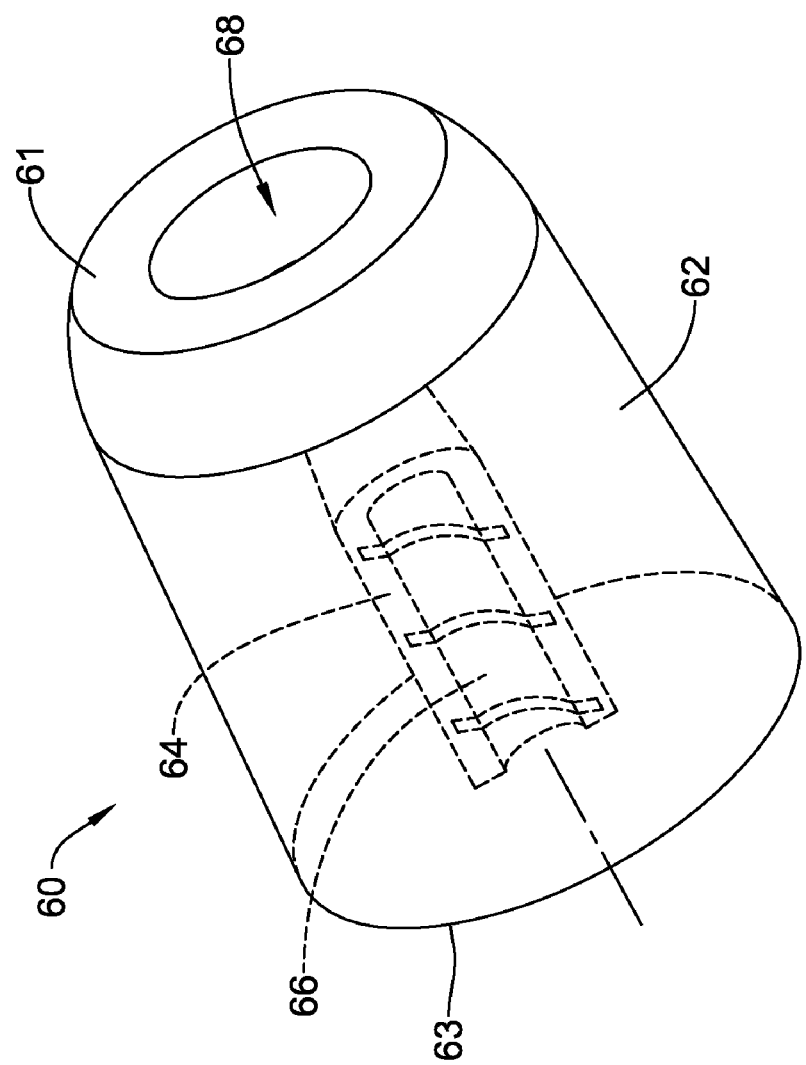
FIG. 3 is a perspective view of a second exemplary earpiece for a sound control device, illustrated as a threaded foam tip for a sound control device.
Figure 4:
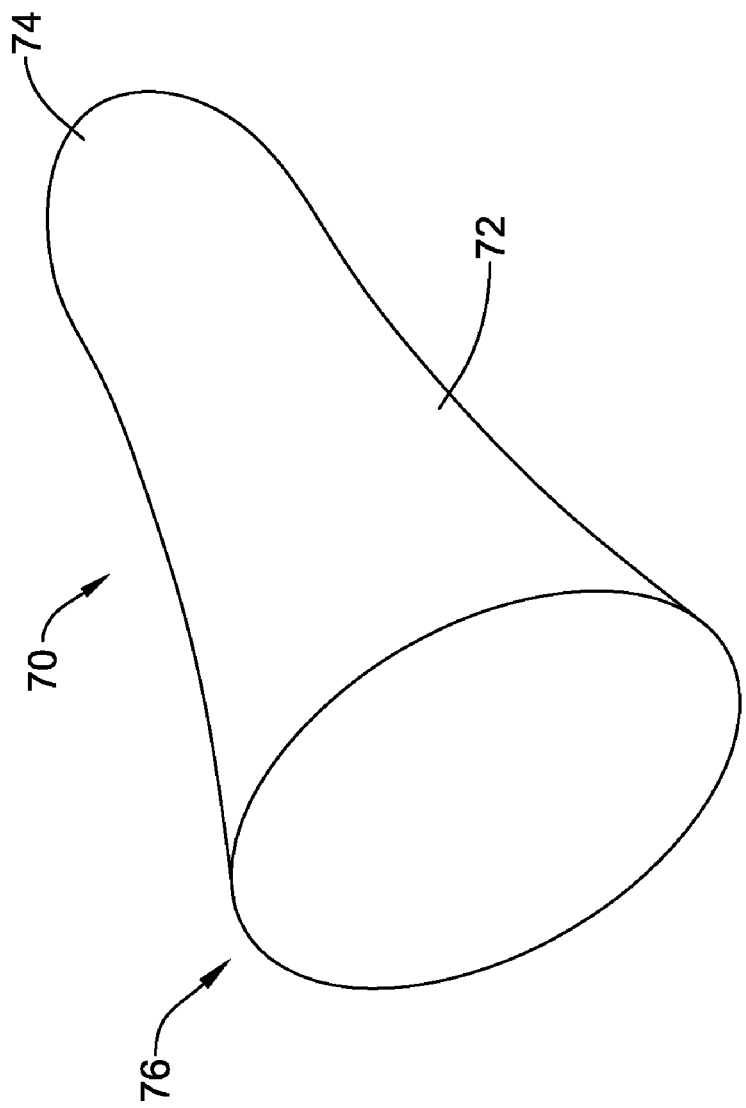
FIG. 4 is a perspective view of a third exemplary earpiece, illustrated as an earplug.

One embodiment of an exemplary foam composition for use in earpieces (e.g., user-disposable foam members), such as foam tips for sound control devices including sound transmission devices and/or earplugs for placement in the ear canal of a user or other earpieces for placement over the ear, on the ear, in the ear, or in the ear canal of a user to seal off unwanted sound from reaching the user's ear drum, or foam sealing material layers for over-the-ear type sound control equipment such as headphones, earmuffs or other hearing protection equipment is illustrated in FIG. 1. FIGS. 2, 3 and 4 illustrate some exemplary embodiments of user-disposable foam members 50, 60 and 70, respectively. Some additional user-disposable foam members for sound control devices are disclosed in U.S. Pat. Nos. 4,880,076, 5,002,151, 5,920,636, 7,236,605 and 7,349,550 and U.S. Pat. App. Pub. No. 2006/0175722, each of which is incorporated herein by reference.

The earpiece 50 shown in FIG. 2 is in the form of a replaceable snap-tip type eartip of a sound control device for insertion into the ear canal of a user. The earpiece 50 may include a body of foam material 52 which may be resiliently compressible into a compressed state for insertion into the ear canal, where it may undergo recovery to a substantial portion of its original size. As the body of foam material 52 undergoes recovery, it may contact and closely conform to the surface of the ear canal, therefore, providing a secure and engaging fit within the ear canal to seal off the canal during use. The earpiece 50 is shown having a generally cylindrical body portion, for example. However, in other embodiments, the earpiece 50 may include other shapes, such as fluted, bulbous, conical, frusta-conical, tapered, convex, concave, or other shaped portions.

The body of foam material 52 may include a lumen 58 extending through at least a portion of the body of foam material 52. In some embodiments, the lumen 58 may extend axially from a first end 51 to a second end 53 of the body of foam material 52. The earpiece 50 may also include a disc or lock ring 54 at one end of the body of foam material 52. The lock ring 54 may be secured to the body of foam material 52, such as adhesively bonded or thermally bonded to the body of foam material 52. The lock ring 54 may include a hole 56 extending therethrough axially aligned with the lumen 58 of the body of foam material 52.

The lumen 58 may be sized and/or configured to receive a connecting portion of a sound control device therethrough. For example, a knob-terminated sound delivery tube of a sound control device may be inserted through the lumen 58 such that the earpiece 50 snaps into place on the sound delivery tube. The knob portion of the sound delivery tube may be passed through the lumen 58 and inserted through the hole 56 of the lock ring 54. The knob portion may be sized slightly larger than the hole 56 such that the knob portion and lock ring 54 form a complementary interlocking fit to hold the earpiece 50 onto the sound delivery tube of the sound control device.

The interlocking fit between the sound control device and the earpiece 50 allows the earpiece 50 to be removably coupled to the sound control device to facilitate replacement of the earpiece 50 when desired. The sound delivery tube may provide a sound conduit to allow desired sound to be transmitted through the earpiece 50 from the sound control device while the earpiece 50 substantially blocks sounds from entering the ear canal other than sounds transmitted from the sound device that pass through the sound conduit.

The earpiece 50 may also include a thin layer of a sound-transmitting material or scrim (not shown) that helps prevent detritus or cerumen from the ear canal from entering a sound delivery tube of a sound device on which the earpiece 50 may be mounted.

The earpiece 60 shown in FIG. 3 is in the form of a replaceable eartip of a sound control device for insertion into the ear canal of a user. The earpiece 60 may include a body of foam material 62 which may be resiliently compressible into a compressed state for insertion into the ear canal, where it may undergo recovery to a substantial portion of its original size. As the body of foam material 62 undergoes recovery, it may contact and closely conform to the surface of the ear canal, therefore, providing a secure and engaging fit within the ear canal to seal off the canal during use. The earpiece 60 is shown having a generally cylindrical body portion, for example. However, in other embodiments, the earpiece 60 may include other shapes, such as fluted, bulbous, conical, frusta-conical, tapered, convex, concave, or other shaped portions.

The body of foam material 62 may include a lumen 68 extending through at least a portion of the body of foam material 62. In some embodiments, the lumen 68 may extend axially from a first end 61 to a second end 63 of the body of foam material 62. The lumen 68 may be configured to receive an elongate tubular member 64, such as a duct, therein. The elongate tubular member 64 may comprise a polymer, or other suitable material, giving the earpiece 60 sufficient rigidity and/or retention properties. The elongate tubular member 64 may be secured to the body of foam material 62, such as adhesively bonded or thermally bonded to the body of foam material 62. The elongate tubular member 64 may include a lumen 66 extending therethrough. The lumen 66 may be sized and/or configured to receive a connecting portion of a sound control device. In some instances, the elongate tubular member 64 may include a threaded portion configured to be threadedly engaged with a threaded portion of a sound delivery tube of a sound control device, allowing the earpiece 60 to be removably coupled to the sound control device to facilitate replacement of the earpiece 60 when desired. In other embodiments the elongate tubular member 64 may be sized and/or configured to frictionally engage or form an interference fit with the sound delivery tube of a sound control device. The lumen 66 may be in communication with the lumen 68 and the sound delivery tube to provide a sound conduit to allow desired sound to be transmitted through the earpiece 60 from the sound control device while the earpiece 60 substantially blocks sounds from entering the ear canal other than sounds transmitted from the sound device that pass through the sound conduit of the earpiece 60.

The earpiece 70 shown in FIG. 4 is in the form of an earplug for insertion into the ear canal of a user to seal off unwanted sound from reaching the user's ear drum. The earpiece 70 may include a body of foam material 72 which may be resiliently compressible into a compressed state for insertion into the ear canal, where it may undergo recovery to a substantial portion of its original size. As the body of foam material 72 undergoes recovery, it may contact and closely conform to the surface of the ear canal, therefore, providing a secure and engaging fit within the ear canal to seal off the canal during use. The earpiece 70 is shown having a generally frusto-conical shape, however other shapes, such as a cylindrical shape are contemplated. The earpiece 70 has a leading end 74 configured to be inserted into the ear canal, and a trailing end 76 opposite the leading end, which typically is positionable proximate the entrance to the ear canal. In some embodiments, the leading end 74 may be sized smaller than the trailing end 76 to facilitate insertion into the ear canal. In some embodiments, the earpiece 70 may include a core member (not shown) extending through at least a portion of the body of foam material 72. The core member may comprise a polymeric material giving the earpiece 70 sufficient rigidity in some applications. For example, a user may grasp a portion of the core member extending from the body of foam material 72 in order to position the member earpiece 70 in the user's ear canal.

Figure 5:
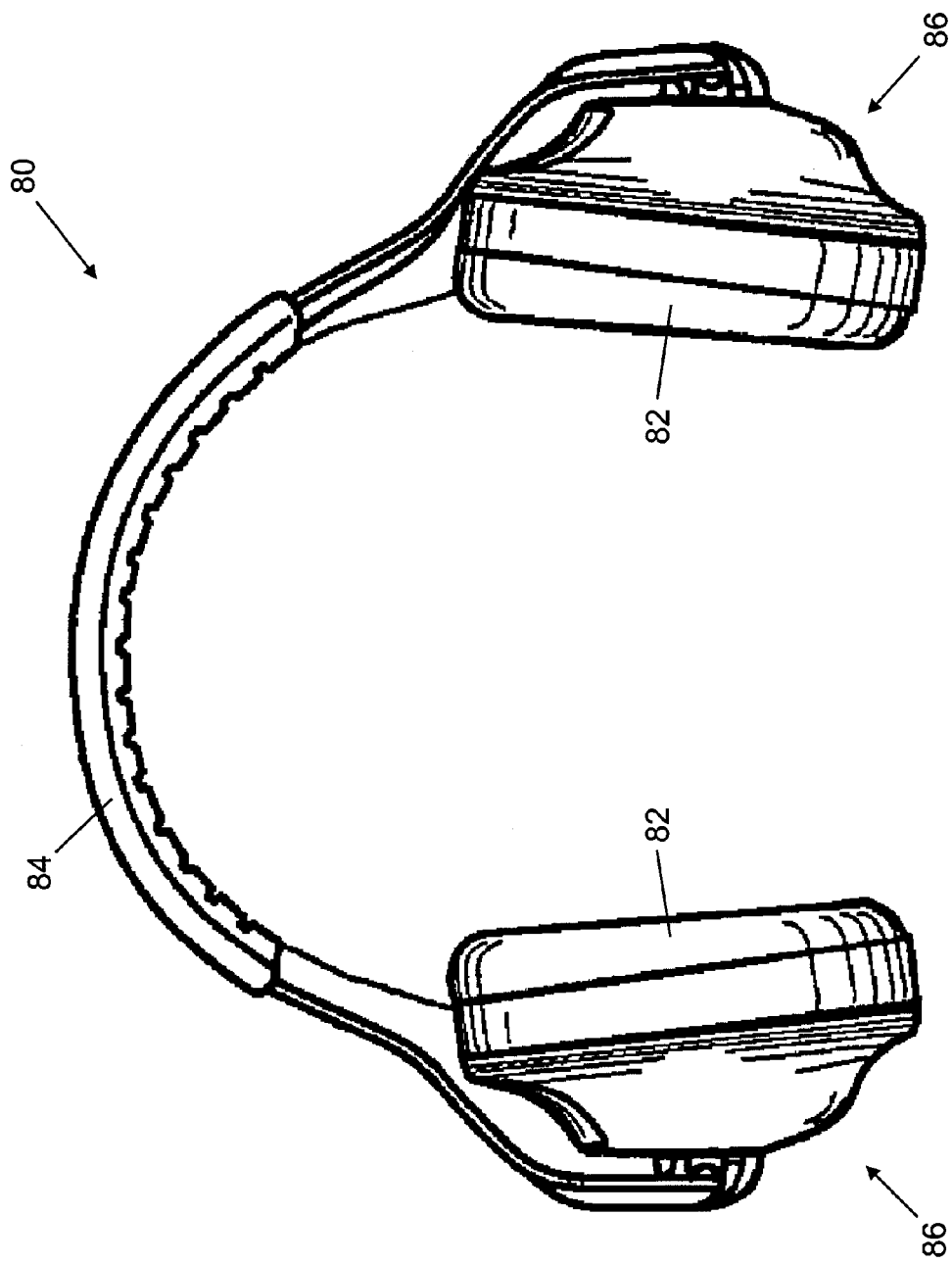
FIG. 5 illustrates a fourth exemplary sound control device, in the form of earphones or earmuffs.

FIG. 5 illustrates an exemplary sound control device, in the form of earphones or earmuffs 80 which may utilize an exemplary foam composition as disclosed herein to provide a sealing layer between the cups 82 of the earphones or earmuffs 80 and the head of the user surrounding the user's ears, sealing off unwanted sound from entering the user's ear canal and reaching the user's ear drum. For instance, the over-the-ear type sound control device may include a pair of cups 82 for placement over the ears of a user. Each cup 82 may include a layer of sound attenuating polymeric foam material 10 at an interface between a circumferential rim of the cup 82 and the head of the user to prevent unwanted sounds from reaching the user's ear drums. A headband 84 may extend between and connect the opposing ear units 86 of the earphones or earmuffs 80 and provide a resilient force to urge the cups 82 into contact with the head of the user to help retain the earphones or earmuffs 80 on the user's head. The headband 84 may be curved to conform around a portion of the user's head.

The polymeric foam material 10 may have a plurality of cells 20 defined by cellular walls 30 of the polymeric foam material 10. The polymeric foam material 10 may include pores 40 extending through cellular walls 30 of the polymeric foam material 10, interconnecting one cell 20 with an adjacent cell 20 of the polymeric foam material 10.

The size of the pores 40 may be less than the size of the cells 20 interconnected by the pores 40. In some embodiments, the polymeric foam material 10 may be an open cell foam or the polymeric foam material 10 may be a closed cell foam. In some embodiments, a majority of the cells 20 of the polymeric foam material 10 are open cells interconnected to adjacent cells 20 by pores 40. In some instances, the polymeric foam material 10 may include 70% or more, 80% or more, 85% or more, 90% or more, or 95% or more open cells.

Although not wanting to be bound by any particular theory, it is believed that the sound attenuation properties of the polymeric foam material 10 may be improved by creating smaller pores 40 between adjacent cells 20 on a consistent basis. The inventors of the current application have determined that as the pore size is decreased, the attenuation of the foam increases, subject to limitations of air flow. Thus, it is believed that there is a relationship between the size of the pores 40 and the volume of the cells 20 that affects the attenuation properties of the polymeric foam material 10.

The inventors of the current application have determined there is a correlation between the pore size and the cell size of a polymeric foam material for determining the attenuation of the polymeric foam material which may be derived by a modification of Bernoulli's Equation for pressure drop across an orifice as follows:

$$\text{Delta } P = \frac{(\rho)(16)(Q^2)}{(\pi)^2}(1/D_2^4 - 1/D_1^4)$$

Where:
Delta P=Attenuation converted into Pascals
$\rho$=density of air @ 20 deg C=1.2041 kg/m$^3$
$D_2$=pore diameter in microns
$D_1$=cell diameter in microns
Q=flow rate of air through pore into cell
Conversion of dB reading into pressure in Pascals is as follows:

$$dB = 20 \text{ Log}(P_1/2.0 \times 10^{-5})$$

Where $P_1$=pressure drop due to the attenuation of sound

The cells 20 in the polymeric foam material 10 may have an average diameter of between about 25 microns to about 250 microns, about 20 microns to about 200 microns, about 25 microns to about 200 microns, about 25 microns to about 100 microns, about 50 microns to about 250 microns, about 50 microns to about 200 microns, about 50 microns to about 75 microns, about 60 microns to about 75 microns, or about 100 microns to about 200 microns. The average diameter of the cells 20 may be about 25 microns, about 50 microns, about 100 microns, about 150 microns, about 200 microns or about 250 microns, in some instances. Thus, the average volume of the cells 20 in the polymeric foam material 10 may be about 8,177 microns$^3$ to about 8,177,000 microns$^3$ or about 8,000 microns$^3$ to about 8,000,000 microns$^3$. In some instances, however, the average volume of the cells 20 in the polymeric foam material 10 may be in the range of about 2,500 microns$^3$ to about 18,000,000 microns$^3$. In some instances the average volume of the cells 20 in the polymeric foam material 10 may be about 10,000 microns$^3$, 50,000 microns$^3$, 100,000 microns$^3$, 250,000 microns$^3$, 500,000 microns$^3$, 1,000,000 microns$^3$, 2,000,000 microns$^3$, 3,000,000 microns$^3$, 4,000,000 microns$^3$, 5,000,000 microns$^3$, 6,000,000 microns$^3$, 7,000,000 microns$^3$ or 8,000,000 microns$^3$.

It may also be desirable that the mode cell diameter (i.e., the size that occurs most frequently in the polymeric foam material) of the polymeric foam material be within the ranges listed above, such as between about 25 microns to about 250 microns, about 20 microns to about 200 microns, about 25 microns to about 200 microns, about 25 microns to about 100 microns, about 50 microns to about 250 microns, about 50 microns to about 200 microns, about 50 microns to about 75 microns, about 60 microns to about 75 microns, or about 100 microns to about 200 microns. The mode diameter of the cells 20 may be about 25 microns, about 50 microns, about 100 microns, about 150 microns, about 200 microns or about 250 microns, in some instances. Thus, the mode volume of the cells 20 in the polymeric foam material 10 may be about 8,177 microns$^3$ to about 8,177,000 microns$^3$ or about 8,000 microns$^3$ to about 8,000,000 microns$^3$. In some instances, however, the mode volume of the cells 20 in the polymeric foam material 10 may be in the range of about 2,500 microns$^3$ to about 18,000,000 microns$^3$. In some instances the mode volume of the cells 20 in the polymeric foam material 10 may be about 10,000 microns$^3$, 50,000 microns$^3$, 100,000 microns$^3$, 250,000 microns$^3$, 500,000 microns$^3$, 1,000,000 microns$^3$, 2,000,000 microns$^3$, 3,000,000 microns$^3$, 4,000, 000 microns$^3$, 5,000,000 microns$^3$, 6,000,000 microns$^3$, 7,000,000 microns$^3$ or 8,000,000 microns$^3$.

Measurements of the size of the cells 20 may be made using methods such as optical microscopy and x-ray micro tomography. Additionally, 3-D imaging techniques, such as stereology techniques, may also be used to measure the size of the cells 20 of the polymeric foam material 10. Alternatively, the equation above may be used, solving for cell diameter ($D_1$), while knowing the measured average pore diameter of the polymeric foam material, the flow rate of air through the polymeric foam material, and the measured attenuation of sound of the polymeric foam material.

The pores 40 may have an average diameter of less than about 60 microns, less than about 50 microns, less than about 40 microns, less than about 30 microns, or less than about 20 microns. The average diameter of the pores 40 may be about 5 microns to about 50 microns, about 10 microns to about 50 microns, about 10 microns to about 40 microns, about 10 microns to about 30 microns, about 30 microns to about 60 microns, or about 30 microns to about 50 microns in some instances.

It may also be desirable that the mode pore diameter (i.e., the size that occurs most frequently in the polymeric foam material) of the polymeric foam material be within the ranges listed above, such as less than about 60 microns, less than about 50 microns, less than about 40 microns, less than about 30 microns, or less than about 20 microns. The mode diameter of the pores 40 may be about 5 microns to about 50 microns, about 10 microns to about 50 microns, about 10 microns to about 40 microns, about 10 microns to about 30 microns, about 30 microns to about 60 microns, or about 30 microns to about 50 microns in some instances.

Measurements of the size of the pores 40 may be made using an instrument called a mercury intrusion porosimeter using a test method based on ISO Standard 15901-1. The mercury intrusion technique is based upon the fact that a non-wetting fluid, such as mercury, will not penetrate into pores (or voids) of a porous material unless acted upon by a pressure large enough to cause intrusion. The equation governing this behavior and the working equation in mercury porosimetry is the Washburn equation:

$$d = \frac{-4\gamma\cos\Theta}{P}$$

Where d is the pore diameter, $\gamma$ is the surface tension of the intrusion fluid, $\Theta$ is the contact angle formed by the intrusion fluid on the solid, and P is the applied pressure to the intrusion fluid. The surface tension of mercury is taken as a constant, and the contact angle formed by mercury on a wide array of solids has been shown to be approximately 140 degrees. Surface tension of mercury is given as 480.0 erg/cm$^2$. Knowing these values allows the applied pressure to be related to the diameter of the pore. Quantachrome Instruments of Boynton Beach, Fla. is one possible source for acquiring pore size measurements. Other methods such as optical microscopy and x-ray micro tomography may also be used to measure the size of the pores 40 of the polymeric foam material 10.

The mode values of the pore diameter and cell diameter of the polymeric foam material 10 may more closely represent the characteristics exemplified by the polymeric foam material 10 as a whole. In some instances, the mode values may be substantially similar to the average values of the pore and cell diameters, however, in other instances the polymer foam material 10 may have a distribution of pore and/or cell diameters which shifts the mode values away from the average values.

Accordingly, the polymeric foam material 10 may have a ratio of the mode and/or average diameter of the pores 40 to the mode and/or average diameter of the cells 20 of between 0.02 to 0.2, between 0.05 to 0.2, between 0.1 to 0.2, between 0.02 to 0.1, or between 0.02 to 0.05, in some instances. In other instances, the ratio of the mode and/or average diameter of the pores 40 to the diameter of the cells 20 may be between 0.02 to 0.75, or between 0.02 to 0.5, or between 0.2 to 0.75, or between 0.2 to 0.5.

Furthermore, the polymeric foam material 10 may have a foam density of between 0.10 gm/cm$^3$ to 0.25 gm/cm$^3$, 0.10 gm/cm$^3$ to 0.20 gm/cm$^3$, 0.10 gm/cm$^3$ to 0.15 gm/cm$^3$, 0.15 gm/cm$^3$ to 0.25 gm/cm$^3$, 0.15 gm/cm$^3$ to 0.20 gm/cm$^3$, or 0.20 gm/cm$^3$ to 0.25 gm/cm$^3$, in some instances.

The polymeric foam material 10 may be formed in various manners. For instance, the polymeric foam material 10 may be formed by combining a diisocyanate with a polyol, blowing agent, and catalyst mixture to react and form a polyurethane foam or combining a reactive system of another polymeric mixture with a blowing agent to form a polymeric foam material. Foams may also be formed by an extrusion process, such as the extrusion process utilized by Expancel of Stockviksverken, Sweden, in which a blowing agent (e.g., a hydrocarbon) is encapsulated in a thermoplastic shell. Upon heating, the thermoplastic shell softens and the pressure within the thermoplastic shell from the hydrocarbon increases, resulting in an expansion of the thermoplastic shell. Another extrusion process, described by Huntsman Smartlite, which utilizes a coating on a thermoplastic polyurethane resin and a blowing agent to form polymeric foam may also be used. Other extrusion processes, such as those using carbon dioxide in a critical point extrusion process, may also be used. In other instances, the polymeric foam material 10 may be formed with a plastisol and a blowing agent foamed and fused in a PVC type foam.

In some instances, the polymeric foam material 10 may be formed by incorporating a blowing agent that decomposes to liberate a gas, mechanically whipping a gas or vaporizable liquid into a polymeric mixture, or adding a water soluble salt or a solvent extractable agent to a polymeric mixture prior to forming, then leaching out the agent after the forming process, leaving voids in the formed material. It is contemplated that other processes may be utilized in forming the polymeric foam material 10.

Although other compositions are contemplated, in some instances the polymeric foam material 10 may be an open cell polyurethane foam made by reacting a diisocyanate, such as methylene diphenyl diisocyanate (MDI), for instance the Argus Prepolymer supplied by Filtrona Corporation of Milton Keynes, England, with a polyol mixture, such as the Argus Polyol mixture supplied by Filtrona Corporation of Milton Keynes, England, in the presence of a catalyst mixture, such as the Argus Catalyst mixture supplied by Filtrona Corporation of Milton Keynes England. In some instances, the polymeric mixture has an isocyanate index in the range of between 92 and 104. The isocyanate index is equal to the actual amount of isocyanate used in the mixture divided by the theoretical amount of isocyanate required for a complete reaction with the mixture multiplied by 100.

The size of the pores 40 of the polymeric foam material 10 may be reduced by the use of a filler added to the polymeric composition. Without being bound by a particular theory, it is believed that the filler acts to reinforce the cell wall 30 and reduces the size of the pore 40 that is formed when the cell wall 30 ruptures, either during the foam forming process, or as a consequence of a post-forming processing step. It is believed that controlling the volume fraction of the filler added to the foam reaction mixture, the bond between the filler particle and the foam reaction mixture, the size of the filler particles, and/or the type of filler used contributes to the enhanced attenuation properties of the polymeric foam material 10. The inventors, through experimental observations, have evidenced that the inclusion of a filler may form more closed cells than similar polymeric mixtures not including a filler. As the gas cools in the closed cells after the reaction is completed, the gas in the closed cells creates a partial vacuum, causing the closed cells to be compressed by atmospheric pressure and rupturing the cellular walls of closed cells. The inventors have observed that crushing the polymeric foam material 10 which includes a filler creates more open cells in a controlled fashion, resulting in fewer closed cells being ruptured in an uncontrolled fashion due to atmospheric pressure.

In some instances, the filler may include solid, hollow, fiber-like, platelike, or porous particles. The filler may have an average particle size of about 0.1 microns to about 100 microns, about 10 to about 40 microns, or about 20 to about 40 microns, in some instances. The volume fraction of the filler may be about 0.075 to about 0.225, about 0.1 to about 0.2, or about 0.15. In some embodiments, the filler particles may be nano-sized particles, having an average particle size of between 1 and 100 nanometers.

Some exemplary manmade fillers which may be used include glass beads such as those available from Potters Industry Spheriglass as A3000CP01 and CP03, glass bubbles such as those available from Potters Industry Spheriglass as Q-Cel 6014, ceramic beads such as those available from 3M as Zeeospheres, phenolic bubbles, porous beads such as those known as Aerogel VM 2270, and porous starch particles such as those available from Medafor as Microporous Polysaccharide Hemospheres (MPH)

Some exemplary natural fillers which may be used include barium sulfate, calcium carbonate, talc, wollastonite, mica, boron nitride, silicon carbide, and diatomaceous earth, or other particles of various shapes.

Although it is generally understood by those of skill in the art that the inclusion of a filler material frequently stiffens the polymeric foam material, experiments by the inventors have surprisingly shown that the use of glass beads, such as those available from Potters Industry Spheriglass as A3000CP01 and CP03, actually made the polymeric foam material softer to the touch.

Figure 1A:
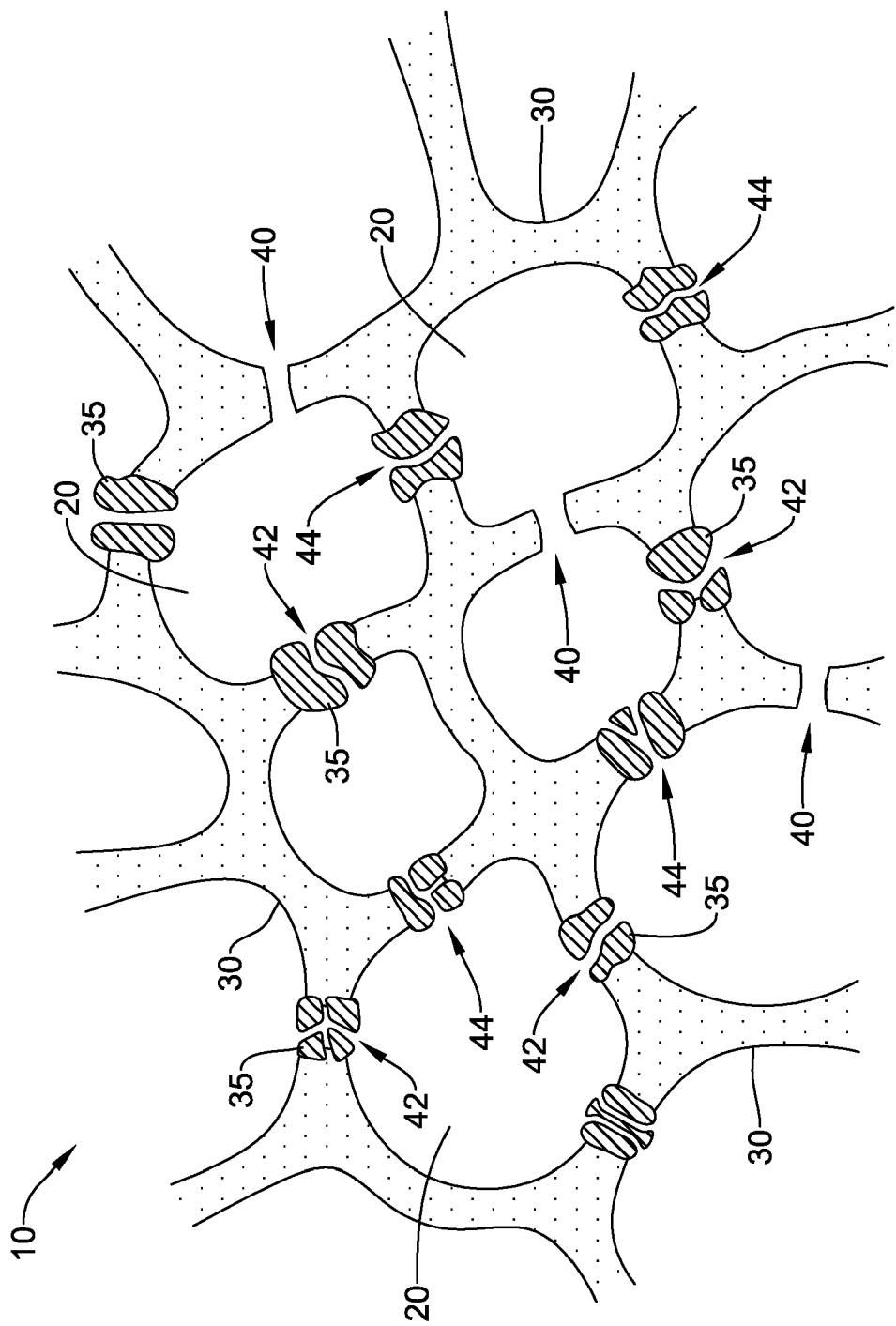
FIG. 1A is a schematic cross-section of a polymeric foam material including filler particles having a channel running continuously through the filler particles which are embedded in the cell walls to form pore openings through the cell walls to interconnect adjacent cells.

In some instances, such as shown in FIG. 1A, the filler may include particles 35 having a channel 42 running continuously through the filler particles 35 such that when the filler particles 35 are embedded in the cell wall 30 the channel 42 through a particle extends between one cell 20 and an adjacent cell 20, thus forming a pore opening 44 through the cell wall 30 between adjacent cells 20.

In other embodiments, microspheres, such as EXPANCEL microspheres sold by Expancel of Stockviksverken, Sweden, may be mixed with a polymer composition to form the polymeric foam material 10, for example, in an extrusion process. Thus, the microspheres may form the cells 20 of the polymeric foam material 10. Openings may be formed in the wall of the microspheres to interconnect the individual cells 20 formed by the hollow interior of the microspheres.

It has been found that forming a sufficient bond between the filler and the polymer material may be desirable (e.g. a bond strength equal to or greater than van der Waals forces), otherwise the filler may tend to weaken the cell walls 30 of the polymeric foam material 10. In some instances, a coupling agent may be added to the reaction mixture with the filler to provide a bond, such as a covalent bond, between the filler and one or more of the polymers of the reaction mixture. In other instances, the coupling agent may be coated onto the filler particles before the filler is added to the reaction mixture. In some embodiments, the coupling agent may be a silane, such as amino-silanes, methacrylsilanes, hexamethyldisilanes, ureidopropyltriethoxysilanes, glycidyloxypropyltrimethoxysilanes, mercaptopropylmethyldimethoxysilanes, diaminoalkylfunctional silanes, isocyanatosilanes, alkylalkoxysilanes, vinylfunctional silanes, organosilicone silanes and epoxyfunctional silanes, or combinations thereof.

In some embodiments, the polymeric foam material 10 may have a percent of open cells in the range of about 70% to about 100%, or in the range of about 80% to about 100%. In some instances, the percent of open cells may be in the range of about 70%, about 75%, about 80%, about 85%, about 90%, about 95%, or about 100%. Measurements of the percent of open cells of the polymeric foam material 10 may be made using an instrument called a gas pycnometer using a test method based on ASTM Standard D6226. Quantachrome Instruments of Boynton Beach, Fla. is one possible source for acquiring measurements of the percent of open cells in the polymeric foam material 10.

If desired, the cell walls 30 of the polymeric foam material 10 may be ruptured in a controlled manner subsequent to the reaction process to form and/or alter pores 40 between adjacent cells 20 of the polymeric foam material 10. For instance, controlled crushing of the polymeric foam material 10 may be used to controllably form pores 40 of a size that enhances the sound attenuation properties of the polymeric foam material 10. The inventors have found that crushing may be performed between 1 to 60 minutes from the start of the foaming reaction to achieve desired results. The inventors have observed that some degree of controlled crushing up to a threshold level improves the sound attenuation performance, however, progressing beyond this threshold level will result in adverse effects on attenuation. The degree of crushing below this threshold level relates inversely to sound attenuation performance. The polymeric foam material 10 may be crushed by compressing the thickness of the polymeric foam material 10 to a thickness which is in the range of about 30% to about 60% of its original thickness. For instance, the polymeric foam material 10 may be controllably crushed to a thickness which is in the range of about 30%, about 35%, about 40%, about 45%, about 50%, about 55%, or about 60% of its original thickness. One possible technique which may be used to crush the foam may be to pass the foam material between two rotating rolls set a specified distance apart which apply a controlled amount of compression to the foam material.

Air flow through the polymeric foam material 10 may be in the range of about 20 ml/min to about 80 ml/min, about 20 ml/min to about 60 ml/min, about 20 ml/min to about 40 ml/min, or about 20 ml/min to about 30 ml/min. For instance, the air flow through the polymeric foam material 10 may be about 20 ml/min, about 30 ml/min, about 40 ml/min, about 50 ml/min, about 60 ml/min, about 70 ml/min or about 80 ml/min. Air flow measurements may be determined according to ASTM test standard D3574-05. Air flow measurements acquired by Hearing Components, Inc., and provided herein, are based on ASTM D3574-05, except that the vacuum chamber containing the foam sample was modified to accept a smaller sample of foam, the sample having a cross-sectional area of about 0.71 in$^2$.

It is also desirable that the polymeric foam material 10 maintains a level of softness or compliance, as measured by the compressional modulus of the polymeric foam material 10, as described herein. In some embodiments, the polymeric foam material 10 may have a compressional modulus in the range of about 0.5 psi to about 4.5 psi or in the range of about 0.5 psi to about 3.5 psi measured at 37 degrees Celsius and 50% relative humidity. Unlike a rigid foam material, the polymeric foam material 10 may be sufficiently flexible to conform to a contoured portion of a user's anatomy, such as the outer ear, the concha of the ear, the ear canal, another region of the ear, or region of the head surrounding the ear.

Furthermore, it may be desirable that the polymeric foam material 10, which may be a slow recovery foam, has a recovery time, as described herein, in the range of 1 second to 60 seconds measured at 37 degrees Celsius and 50% relative humidity. Although it is common for slow recovery foams to lose their slow recovery features when saturated in water, the polymeric foam material 10 may retain at least a portion of its slow recovery time when saturated in water.

The following table provides some possible ranges of properties of the polymeric foam material 10.

| Property | Unit | Range |
| --- | --- | --- |
| Mean/Mode Pore Diameter | micron | 10-50 |
| Mean/Mode Cell Diameter | micron | 25-250 |
| Foam Density | gm/cm$^3$ | 0.10-0.25 |
| Percent Open Cell | percent | 70-100 |
| Crush | percent | 30-60 |
| Filler Particle Size | micron | 0.1-100 |
| Filler Volume Fraction | fraction | 0.075-0.225 |
| Compressional Modulus @ 37° C., 50% RH | psi | 0.5-4.5 |
| Recovery Time @ 37° C., 50% RH | second | 1-60 |
| Air Flow | ml/min | 20-80 |

TEST METHODS

Sound Attenuation

The basic test method for measuring the sound attenuation of foams was internally developed by Vasant Kolpe at Hearing Components, Inc. The method utilizes a piece of test equipment called the Frye Electronics Fonix 6500 Hearing Aid tester along with a modified HA-1 coupler. The sound chamber of the Fonix 6500 is placed inside an oven and the attenuation measurement is made at 98 degrees Fahrenheit. The details of the test procedure are as follows.

Attenuation Test Procedure—Composite Mode:
1.1 Turn on the Fonix® Test System, the computer monitor, the oven, and the thermometer, press the reset button on the Fonix control panel.
1.2 Prop the lid of the Frye sound chamber open inside the oven so the temperature stabilizes quicker.
1.3 Place the wireless temperature/humidity gauge inside the oven.
1.4 Once the temperature is stabilized at 98±3° Fahrenheit, get the baseline by following the procedure for leveling found in the Fonix® 6500 CX Operator's manual, under chapter 7, 7.1.1 ANSI leveling (the procedure has been summarized below).
  1.4.1 Measure thickness of sample. (Sample should be 6.5-7.5 mm thick,)
  1.4.2 Put the dummy microphone in the Attenuation Test Fixture (ATF) and place inside the chamber next to the real microphone.
  1.4.3 Position the real microphone near the center of the box (center is marked by a small circle drawn on the bottom of the chamber).
  1.4.4 Press the "Level" button on the Fonix® 6500 CX.
  1.4.5 Check the monitor to ensure that the setup has been leveled by looking for a flat gain of 0 dB; if not, repeat steps 1.4.2-1.4.4. (a drift of +/−1 dB is allowed).
1.5 Prepare samples of the foam through the freeze cut technique. (Prior to this procedure, a cylinder of the foam sample has been cut by first freezing the foam sample and then using a ⅝ inch cutting die to cut a cylinder of the foam. At least one end of the cylinder is cut at 90 degrees to the main axis of the sample.
  1.5.1 Using the foam cutting fixture, put a small drop of water in the bottom of the 7 mm well.
  1.5.2 Put the foam sample into the 7 mm well. Make sure that the flat end of the sample is all the way down into the well and the sample is standing straight up.
  1.5.3 Place the fixture in the freezer and allow the foam to harden.
  1.5.4 After the foam has frozen, use a razor blade to cut away the foam sticking out of the fixture, leaving a 7 mm disk of foam behind.
  1.5.5 Samples should be cylindrical disks with a height of 7 mm. Check the quality of the samples made.
  1.5.6 Mount the sample in the center of the 5 mm spacer and place spacer (5 mm) into the ATF well.
  1.5.7 Insert the microphone into the ATF coupler until it bottoms out in the coupler.
1.6 Press the ATF coupler down into the foam holder slowly to compress the foam until the coupler bottoms out on the 5 mm spacer. Press the coupler slowly to prevent damage to the microphone.
1.7 Place the whole assembly into the test chamber. Seal the coupler vent using fun tack putty and seal around the microphone housing to insure that sound enters the coupler only through the foam using the following procedure.
  1.7.1 Seal the end of the microphone where the cable exits the microphone using the sound insulating putty to cover the end of the microphone housing.
  1.7.2 Cut a piece of VHB tape #4930 about 1.2 inches long and press onto the bottom of a 9/16 inch Ruland 9/16 inch split collar which was adjusted to just loosely fit around the microphone housing.
  1.7.3 Cut a 7/16 inch hole into the #4930 tape using a 7/16 inch punch die.
  1.7.4 Remove the release liner from the tape, slide the microphone through the collar starting from the side that does not contain the #4930 tape until about 0.5 inch of the microphone is protruding below the bottom of the collar.
  1.7.5 Insert the microphone into the ATF coupler until it bottoms out in the coupler.
  1.7.6 Check to insure the microphone has been adequately sealed by placing the 0.23 inch thick silicone rubber sealing piece into the foam holder (which contains the 5 mm spacer).
  1.7.7 Position the silicone rubber sealing piece so that it adequately covers the entrance hole to the ATF coupler.
  1.7.8 Place the AFT coupler into the foam holder containing the silicone seal piece and compress the silicone sealing piece against the ATF coupler until the ATF coupler bottoms out on the 5 mm spacer and tighten the foam holder retaining screws to hold the foam holder onto the ATF coupler keeping the silicone sealing piece compressed against the ATF coupler sealing the hole into the coupler.

1.7.9 Place the ATF coupler assembly into the Frye sound chamber, set the sound pressure level to 90 dB composite noise signal and run a scan 10 x's recording the reading measured by the microphone at 90 dB SPL. The average of these 10 readings must be below 51 dB for the sealing of the coupler to be acceptable.

1.8 With the Frye tester in the composite mode, use the up control arrow to increase the RMS source signal to 90 dB. Press the Menu button, press the I/O button. Use the down control arrow to move the cursor to I/O Delay. Press the "Start" button to begin the Composite Mode measurement.

1.9 Record the Composite Mode value displayed on the right hand side of the screen.

1.10 Calibration measurement—Place the ATF into the Frye test chamber without any foam sample in the fixture (open coupler). Perform a measurement as described in 1.8 to obtain the Composite Mode value with an open coupler.

1.11 To obtain the Composite Mode attenuation, subtract the Composite Mode value obtained with the foam sample in the ATF from the Composite Mode calibration value.

Attenuation Test Procedure—Pure Tone Mode:

Follow the steps 1.1-1.7, provided above for composite mode.

1.8 Place the Fonix 6500 into the pure tone mode by pressing the reset button on the control panel and then press the sine/composite button on the control panel.

1.9 Set noise reduction to 4 by pressing the noise reduction button twice on the control panel.

1.10 Increase the sound pressure level in the sound chamber to 100 dB by pressing the up arrow switch on the control panel until 100 dB is displayed.

1.11 Set the starting frequency to 200 Hz by pressing the left facing arrow switch on the control panel until 200 Hz is displayed.

1.12 Press the start button to run a scan from 200 Hz to 8000 Hz.

1.13 Record the results.

1.14 Calibration is run the same as described above except without any foam sample in the coupler foam holder.

1.15 To obtain the Pure Mode attenuation, subtract the Pure Mode value obtained with the foam sample in the ATF from the Pure Mode calibration value.

Composite Mode vs. Pure Tone

The Standard Composite signal is composed of 79 different individual frequencies that are each generated with a random phase pattern that results in the signal having a crest factor of 10 dB, close to the crest factor of human speech. (If the phase components were not randomized or otherwise changed, and if all the signal components were in phase, the crest factor of the signal would increase to over 19 dB.) The Standard Composite signal is the standard signal used on the 6500-CX test system, the predecessor to the 7000. The crest factor of a waveform is the ratio of its highest amplitude to its RMS amplitude. Human speech is often referred to as having a 12 dB crest factor.

A pure-tone sweep is a test involving a progression of pure tone signals presented at a specified level. When the sweep is complete, the measured signal values at those frequencies are displayed on the graph (or data column). Pure Tone Sweep: Contains 64 different frequencies and only does one sweep before ending the test. Noise reduction is used in noisy testing environments. Pure-tone noise reduction takes several measurements at each frequency and averages those measurements together. Larger noise reduction numbers lead to smoother curves but increase the amount of time it takes to complete a pure-tone sweep. For example, if you select "4" as the pure-tone noise reduction setting, 256 measurements (64×4) will be taken with every pure-tone sweep.

Compressional Modulus/Recovery Time Test

The compressional modulus/recovery time test method was an internally developed test method. The details of the test procedure are as follows.

Foam samples are prepared by taking the foam sample and freezing it. After freezing, a ⅝ inch cutting die is used to cut a cylinder of foam from the original sample. This cylinder is then frozen again and then one end is cut at 90 degrees to the main axis of the cylinder, a distance of 15 mm is measured from this first cut surface and then a second 90 degree cut is made forming a cylinder of foam ⅝ inches in diameter and 15 mm long. This sample is then subjected to the following test procedure.

1.1 Condition the foam sample at 50% RH and 37 deg. C. for 24 hrs prior to testing.

1.2 Place the Dillon Quantrol tensile tester in the lab temperature/humidity chamber with the chamber set to a temperature of 37 deg. C. and humidity of 50%.

1.3 Attach the dial indicator to the Dillon Quantrol tensile tester and align vertically.

1.4 Attach the compression plate to the load cell.

1.5 Zero the load cell and select lbf unit for readout.

1.6 Place a foam sample under the compression plate of the load cell and slowly lower the compression plate until it just touches the top of the sample.

1.7 Set the crosshead speed to 12 inch/min.

1.8 Set the dial indicator to zero.

1.9 Compress the foam sample 30% at 12 inch/min. crosshead speed.

1.10 Hold the foam sample in the compressed state for 3 minutes.

1.11 Record the peak force experienced by the foam sample during its compression.

1.12 After three minutes raise the compression plate 80% of the original compression distance and time how long it takes the foam sample to recover to this point. This occurs as the force gauge just begins to register a value above zero.

1.13 The time required for the foam sample to recover the 80% is taken as the recovery time.

1.14 Calculate the compressional modulus by dividing the peak compression force by the cross sectional area of the foam sample.

EXAMPLES

The following table provides some experimental polymeric foam compositions produced by the inventors at Hearing Components, Inc., of Oakdale, Minn. in accordance with this disclosure.

| Sample # | Polyol[1] (weight %) | Prepoly[2] (weight %) | Catalyst[3] (weight %) | Filler Type | Filler Vol Frac | Crush % | Density (gm/cc) |
|---|---|---|---|---|---|---|---|
| 2.3039 | 50.7 | 45.9 | 3.4 | $BaSO_4$ | .07 | 80 | .174 |
| 8.3039 | 50.7 | 45.9 | 3.4 | $BaSO_4$ | .07 | 40 | .178 |
| 3.10148 sec #1[5] | 50.7 | 45.9 | 3.4 | $BaSO_4$ | .05 | 40 | .163 |
| 3.10148 sec #3[5] | 50.7 | 45.9 | 3.4 | $BaSO_4$ | .05 | 80 | .150 |
| 3.1069 | 50.7 | 45.9 | 3.4 | none | 0 | 40 | .14 |
| 8.1069 | 50.7 | 45.9 | 3.4 | A3000cp01 | .17 | 40 | .18 |
| 3.3199 | 50.7 | 45.9 | 3.4 | none | 0 | 40 | .14 |
| 10.3199 | 50.7 | 45.9 | 3.4 | $BaSO_4$ | .06 | 40 | .17 |
| 3.62910 | 50.7 | 45.9 | 3.4 | $BaSO_4$ | .09 | 40 | |
| 4.63010 | 50.7 | 45.9 | 3.4 | None | 0 | 40 | |
| 6.63010 | 50.7 | 45.9 | 3.4 | $BaSO_4$ | .09 | 40 | |

| Sample # | Pore Dia[4,7] (micron) | Cell Vol[6] (cubic micron) | % Open Cell | Attenuation (composite mode) (dB) | Compr. Mod. (psi) | Rec. Time (sec) |
|---|---|---|---|---|---|---|
| 2.3039 | 2.7-420 | $10.4\text{-}3.9 \times 10^7$ | Not measured | 29.5 | 1.44 | 3 |
| 8.3039 | 2.7-420 | $10.4\text{-}3.9 \times 10^7$ | Not measured | 47.8 | 1.69 | 17.5 |
| 3.10148 sec #1[5] | 5-1000 | $10.4\text{-}3.9 \times 10^7$ | 88.5 | 49 | 3.56 | 10 |
| 3.10148 sec #3[5] | 5-1000 | $10.4\text{-}3.9 \times 10^7$ | 89.4 | 26.3 | 2.28 | 6 |
| 3.1069 | | | | 42.6 | 2.25 | 9 |
| 8.1069 | | | | 46.3 | 2.22 | 53.8 |
| 3.3199 | | | | 39.6 | 2.15 | 17 |
| 10.3199 | | | | 45.1 | 3.49 | 19.8 |
| 3.62910 | 30.9 | $9.23 \times 10^4$ | | 48.6[8] | 3.78 | 14.5 |
| 4.63010 | 54.8 | $1.81 \times 10^5$ | | 45.6[8] | 1.97 | 12.5 |
| 6.63010 | 54.7 | $2.18 \times 10^5$ | | 45.2[8] | 2.19 | 27.2 |

[1]Argus Polyol mixture supplied by Filtrona Corporation of Milton Keynes, England
[2]Argus Prepolymer supplied by Filtrona Corporation of Milton Keynes, England
[3]Argus Catalyst mixture supplied by Filtrona Corporation of Milton Keynes, England
[4]Pore diameter data for Samples 2.3039 and 8.3039 came from University of MN Report Jul. 23, 2009 x-ray micro tomography results.
[5]Data for Samples 3.10148 sec #1 and 3.1018 sec #3 came from Quantachrome gas pycnometer results (% open cell) and mercury intrusion porosimetry results (pore size range).
[6]Cell volumes listed in the table are the total range measured. Cell volume was calculated from pore size distributions reported in University of MN Report Jul. 23, 2009 x-ray micro tomography results.
[7]Pore diameters listed in the table are the total range measured.
[8]Step 1.8 of the Attenuation Test Procedure was run using an amplifier to increase the RMS source signal to 100 dB for these samples and the compared commercial samples of FIGS. 8-10.

Experimental polymeric foam materials according to the above disclosure were found to have enhanced sound attenuation by 3 dB or more relative to currently available foam eartips. Increases on the order of 3 dB are generally considered a significant increase in the attenuation of sound energy and correspond to a doubling of the permissible exposure time for an individual working within the sound field and exposed to the sound.

Figure 6:
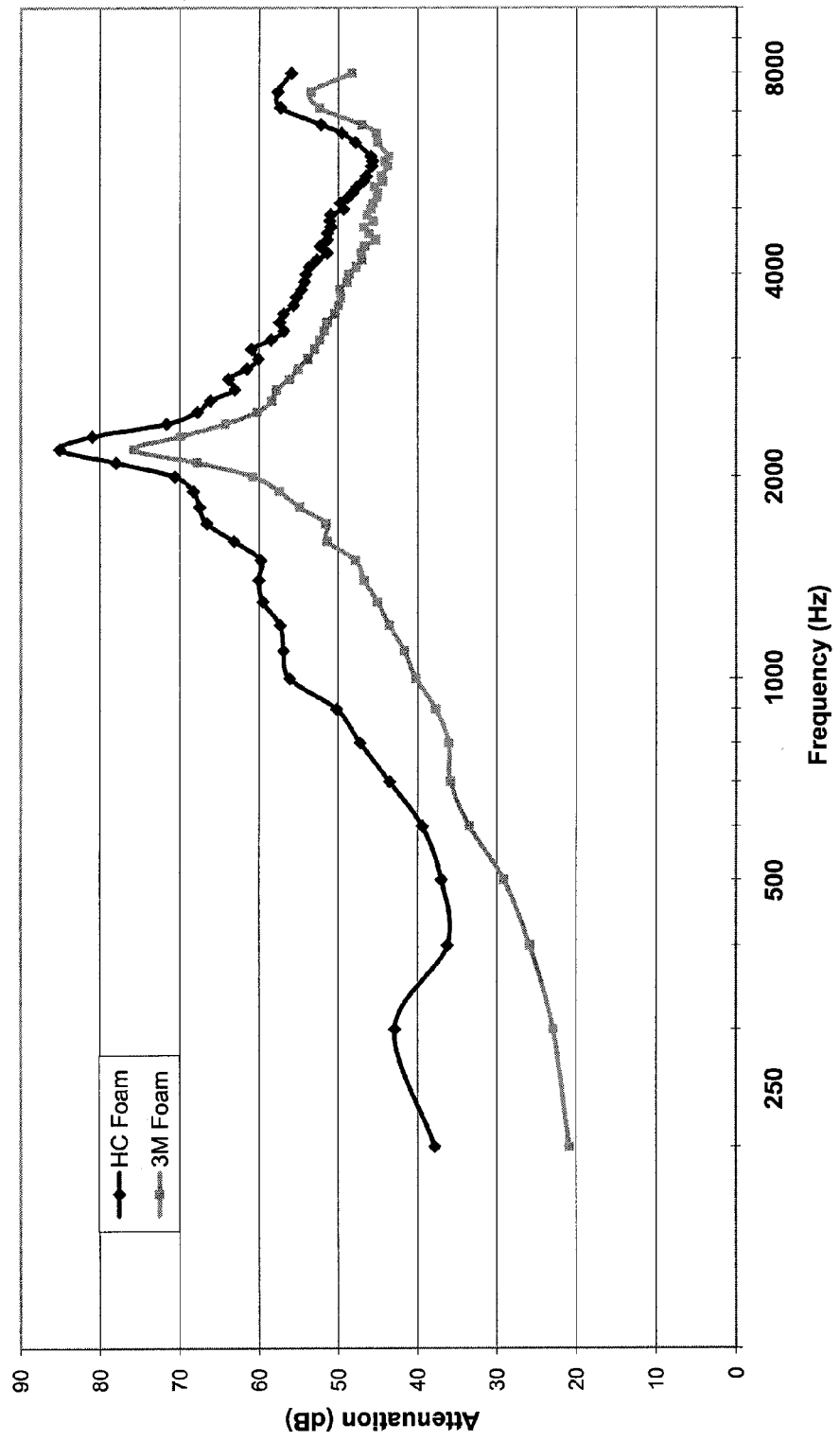
FIGS. 6-10 are charts comparing experimental test samples of a polymeric foam material in accordance with this disclosure to commercially available polymeric foams.
Figure 7:
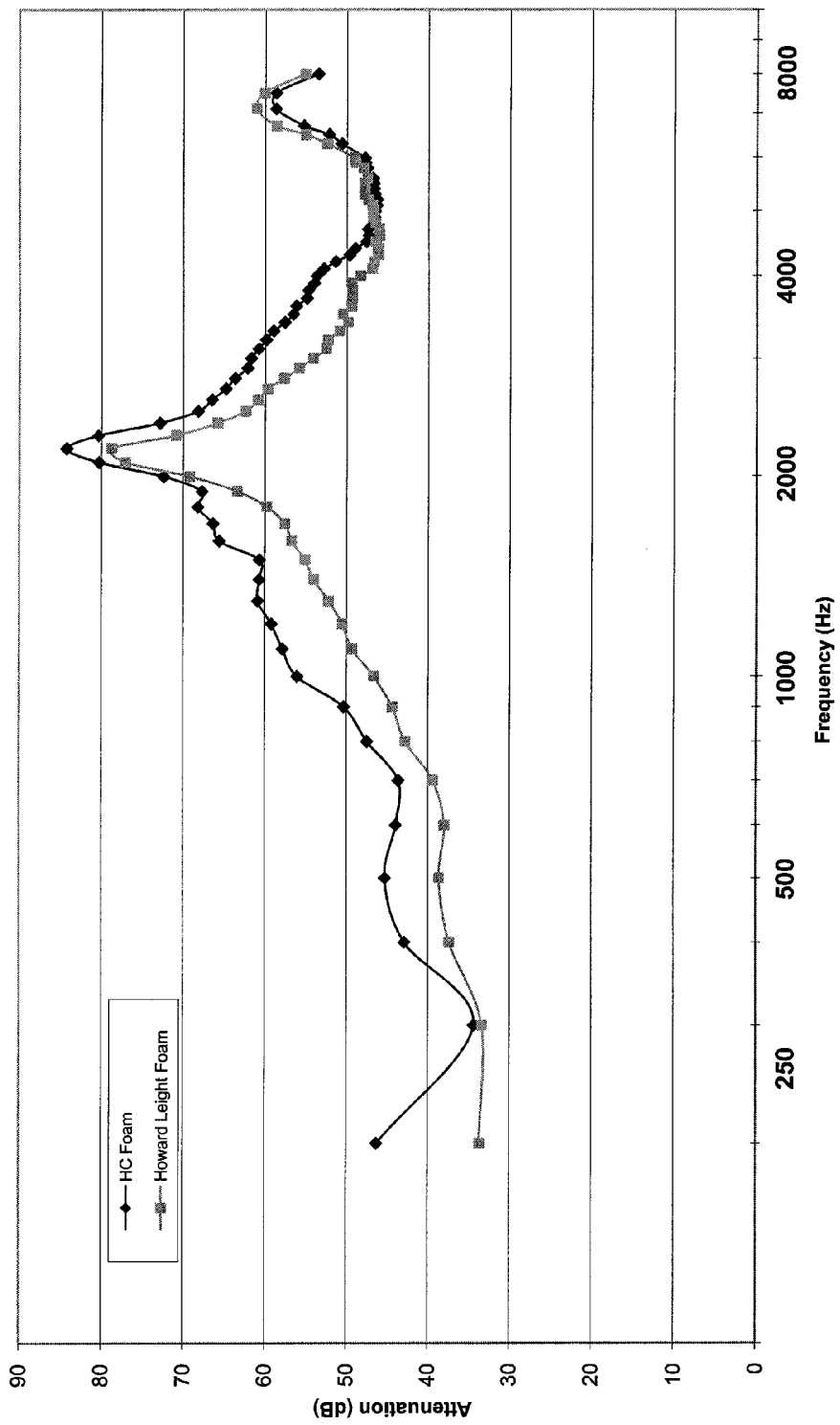

The charts at FIGS. 6 and 7 illustrate a comparison of the sound attenuation properties of experimental polymeric foam materials in accordance with this disclosure formed by the inventors at Hearing Components, Inc. with foam materials currently available from 3M and Howard Leight, respectively. The attenuations shown are based on pure tone measurements. The chart at FIG. 6 is a comparison of a commercially available foam from 3M which is used in the manufacture of eartips currently provided to Hearing Components, Inc. as HC 005.6829.1 (3M Foam) to a sample of polymeric foam material (Sample #9.6049) in accordance with this disclosure (HC Foam). The 3M provided foam material is currently used in Comply® Canal Tips and Comply® T-Series Tips sold by Hearing Components, Inc. The chart at FIG. 7 is a comparison of a commercially available foam from Howard Leight as Howard Light Max, which is used in the manufacture of earplugs, to a sample of polymeric foam material (Sample #4.2119) in accordance with this disclosure (HC Foam). The Howard Leight Max foam has the highest noise reduction rating (NRR) of all foams available from Howard Leight which are known to the inventors. The Howard Leight Max has a published NRR rating of 33.

The following table outlines the composition of the polymeric foam samples produced by the inventors at Hearing Components, Inc., of Oakdale, Minn. included in the accompanying charts of FIGS. 6 and 7.

| Sample # | Polyol[1] (weight %) | PrePoly[2] (weight %) | Catalyst[3] (weight %) | Filler Type | Filler (Vol. Frac.) |
|---|---|---|---|---|---|
| 9.6049 | 50.7 | 45.9 | 3.4 | Solid glass beads having a mean diameter of 35 microns | 0.146 |

-continued

| Sample # | Polyol[1] (weight %) | PrePoly[2] (weight %) | Catalyst[3] (weight %) | Filler Type | Filler (Vol. Frac.) |
|---|---|---|---|---|---|
| 4.2119 | 50.7 | 45.9 | 3.4 | (Potters Industries Spheriglass A3000-CP03) coated with a coupling agent. BaSO$_4$ | 0.066 |

Figure 8:
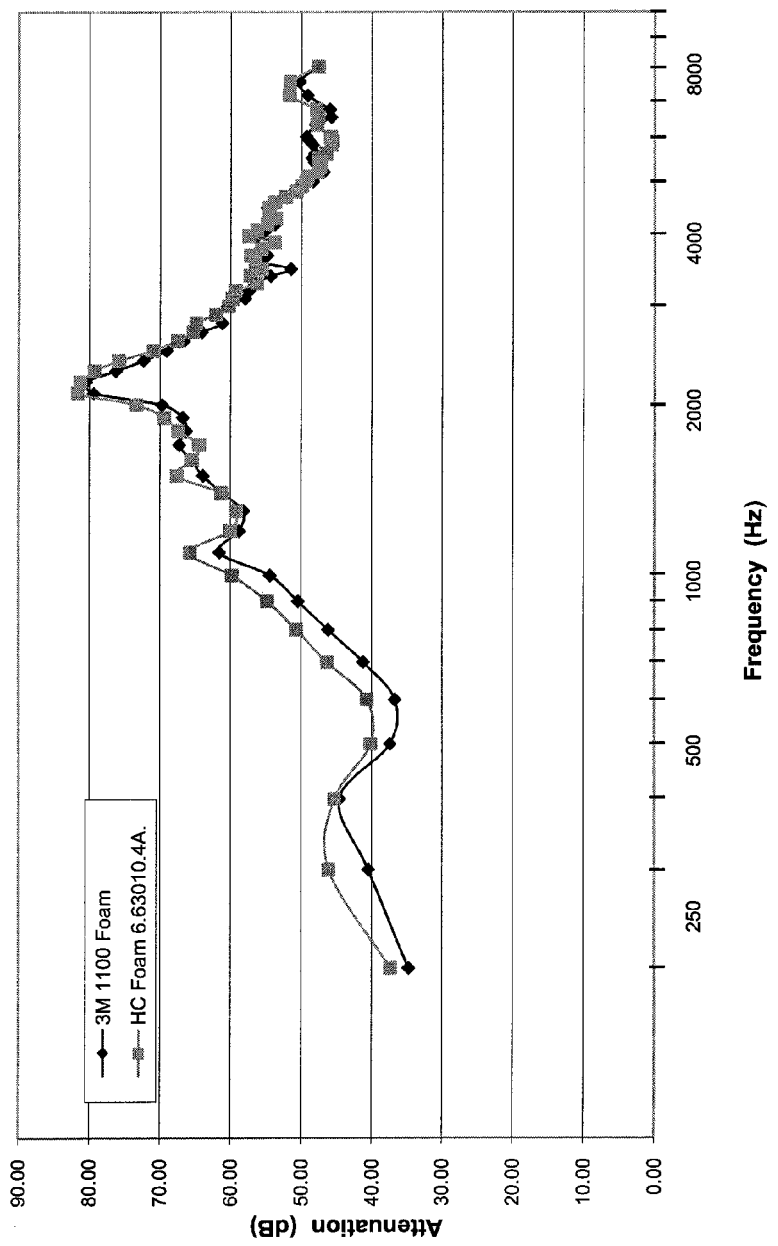
Figure 9:
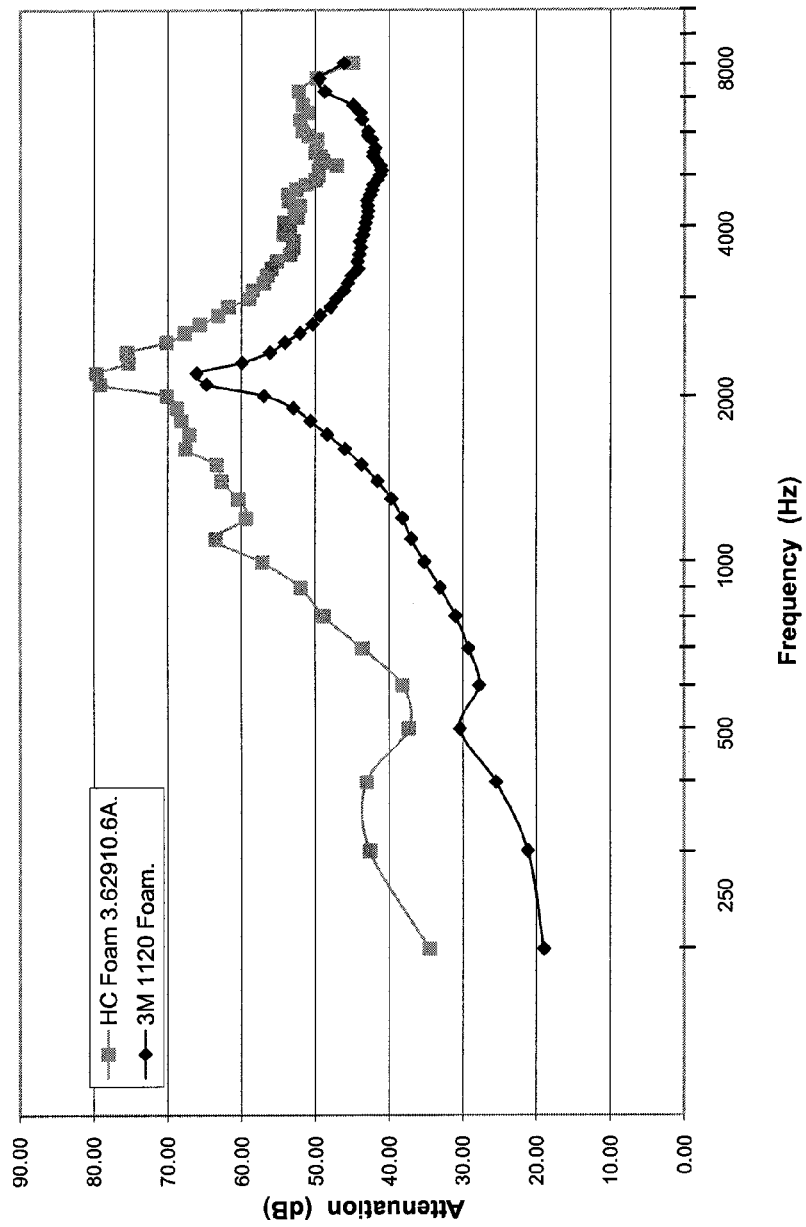

[1]Argus Polyol mixture supplied by Filtrona Corporation of Milton Keynes, England
[2]Argus Prepolymer supplied by Filtrona Corporation of Milton Keynes, England
[3]Argus Catalyst mixture supplied by Filtrona Corporation of Milton Keynes, England The charts at FIGS. 8 and 9 illustrate a comparison of the sound attenuation properties of experimental polymeric foam materials (i.e., samples 3.62910 and 6.63010) in accordance with this disclosure formed by the inventors at Hearing Components, Inc. which were subjected to a controlled crushing step with commercially available foams from 3M used in 3M 1100 and 3M 1120 earplugs.

Figure 10:
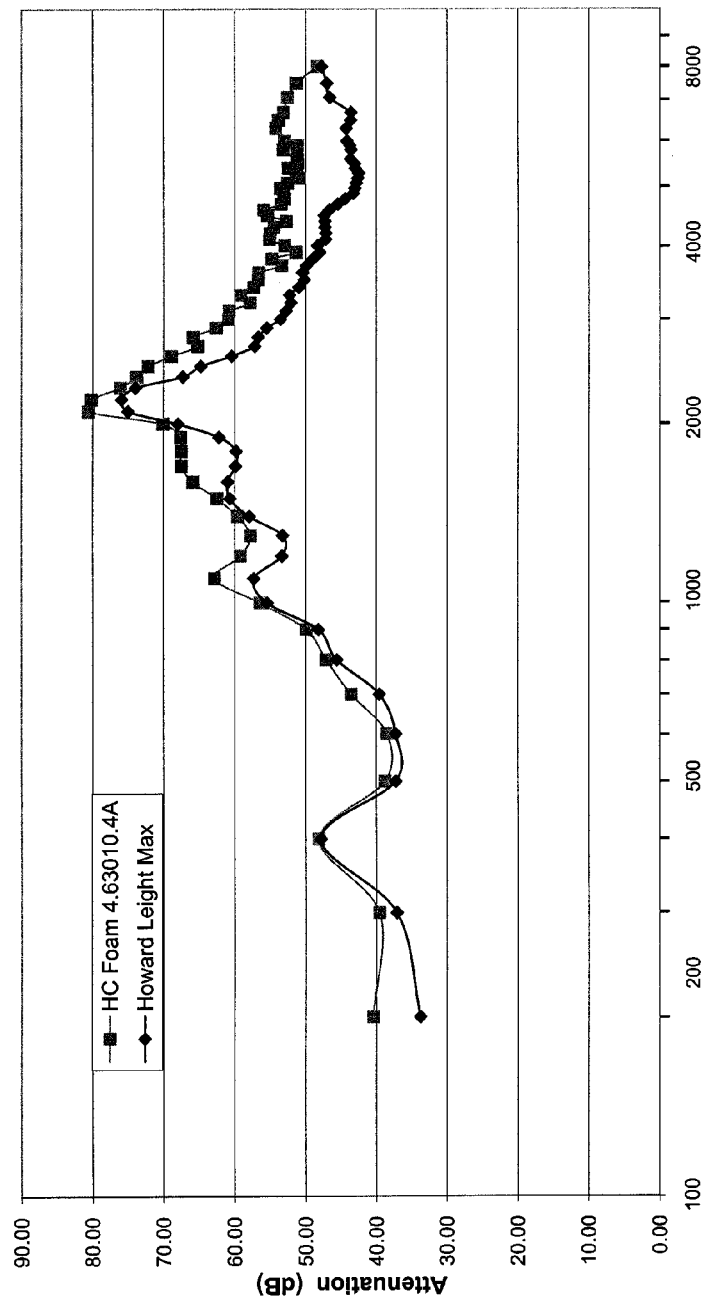

The chart at FIG. 10 illustrates a comparison of the sound attenuation properties of an experimental unfilled polymeric foam material (i.e., no filler particles added) in accordance with this disclosure formed by the inventors at Hearing Components, Inc. which was subjected to a controlled crushing step (Sample #4.63010) with the commercially available foam from Howard Leight known as Howard Light Max, which is used in the manufacture of earplugs. The Howard Leight Max foam has the highest noise reduction rating (NRR) of all foams available from Howard Leight which are known to the inventors. The Howard Leight Max has a published NRR rating of 33. The attenuations shown are based on pure tone measurements.

The following table outlines the composition of the polymeric foam samples produced by the inventors at Hearing Components, Inc., of Oakdale, Minn. included in the accompanying charts of FIGS. 8-10.

| Sample # | Polyol[1] (weight %) | PrePoly[2] (weight %) | Catalyst[3] (weight %) | Filler Type | % Crush |
|---|---|---|---|---|---|
| 3.62910 | 50.7 | 45.9 | 3.4 | BaSO$_4$ | 40 |
| 4.63010 | 50.7 | 45.9 | 3.4 | none | 40 |
| 6.63010 | 50.7 | 45.9 | 3.4 | BaSO$_4$ | 40 |

[1]Argus Polyol mixture supplied by Filtrona Corporation of Milton Keynes, England
[2]Argus Prepolymer supplied by Filtrona Corporation of Milton Keynes, England
[3]Argus Catalyst mixture supplied by Filtrona Corporation of Milton Keynes, England The samples of the competitive commercial foams included in FIGS. 6-10 are the best performing samples of these commercial foams tested by the inventors. It can be seen from FIGS. 6-10 that the samples of polymeric foam material in accordance with this disclosure have enhanced sound attenuation properties relative to those of commercially available polymeric foams used in earpieces, for example, user-disposable foam members such as foam tips for sound control devices including sound transmission devices and earplugs. These commercially available polymeric foams are believed to have widely varying properties. The inventors believe that repeatably controlling the properties and characteristics of the polymeric foam materials in accordance with this disclosure will provide more consistent attenuation characteristics of polymeric foam compositions used in various earpieces.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A sound control device including an earpiece member for placement in close proximity to an ear canal of a user for attenuating sound, the earpiece member comprising:
    a non-reticulated polymeric foam material having a plurality of cells defined by interconnected cellular walls of the polymeric foam material and a plurality of pores extending through the cellular walls between adjacent cells to interconnect adjacent cells of the polymeric foam material;
    wherein the average volume of the cells of the polymeric foam material is between about 8,000 microns$^3$ to about 8,000,000 microns$^3$;
    wherein the average diameter of the pores of the polymeric foam material is between about 5 microns to about 50 microns; and
    wherein a ratio between the average diameter of the pores to an average diameter of the cells is between 0.02 to 0.75.

2. The sound control device of claim 1, wherein the cells of the polymeric foam material have an average diameter between about 25 microns to about 250 microns, and wherein a ratio between the average diameter of the pores to the average diameter of the cells is between 0.02 to 0.2.

3. The sound control device of claim 1, wherein the cells of the polymeric foam material have an average diameter between about 20 microns to about 200 microns, and wherein a ratio between the average diameter of the pores to the average diameter of the cells is between 0.2 to 0.75.

4. The sound control device of claim 1, wherein the polymeric foam material includes a plurality of filler particles embedded in the cellular walls, at least a majority of the filler particles having a channel extending continuously through the filler particle, wherein the channel of at least a portion of the filler particles extends between adjacent cells of the polymeric foam material.

5. The sound control device of claim 4, wherein the channels of the filler particles form the pores between adjacent cells.

6. The sound control device of claim 1, wherein the polymeric foam material includes a plurality of hollow microspheres having spherical walls, interiors of which form at least a portion of the cells, and openings through the spherical walls provide at least a portion of the pores between adjacent cells.

7. The sound control device of claim 1, wherein the polymeric foam material includes a filler material in a volume fraction of between 0.075 to 0.225.

8. The sound control device of claim 1, wherein the polymeric foam material has 80% or more open cells.

9. The sound control device of claim 1, wherein the polymeric foam material is a slow recovery foam having a slow recovery time of between 1 to 60 seconds.

10. The sound control device of claim 9, wherein the polymeric foam material retains at least a portion of the slow recovery time when saturated in water.

11. The sound control device of claim 1, wherein the polymeric foam material is crushed to rupture cellular walls of the polymeric foam material to create at least a portion of the pores between adjacent cells.

12. The sound control device of claim 1, further comprising filler particles dispersed in the polymeric foam material.

13. The sound control device of claim 12, wherein the filler particles are glass beads or bubbles coated with a coupling agent prior to adding the glass beads or bubbles to a reaction mixture for forming the polymeric foam material.

14. A foam earpiece for a sound control device which can be placed in close proximity to the ear canal of a user to attenuate sound, the foam earpiece comprising:
   a non-reticulated polyurethane foam material formed of a polymer mixture of a diisocyanate mixture reacted with a polyol mixture in the presence of a catalyst mixture;
   the polyurethane foam material having a plurality of open cells defined by interconnected cellular walls of the polyurethane foam material and a plurality of pores extending through the cellular walls between adjacent open cells to interconnect adjacent open cells of the polyurethane foam material;
   the polyurethane foam material having a percent of open cells of 80% or more;
   wherein the average volume of the open cells of the polyurethane foam material is between about 8,000 microns$^3$ to about 8,000,000 microns$^3$;
   wherein the average diameter of the pores of the polyurethane foam material is between about 5 microns to about 50 microns; and
   wherein a ratio between the average diameter of the pores to an average diameter of the cells is between 0.02 to 0.75.

15. The foam earpiece of claim 14, wherein the open cells of the polyurethane foam material have an average diameter between about 25 microns to about 250 microns, and wherein a ratio between the average diameter of the pores to the average diameter of the open cells is between 0.02 to 0.2.

16. The foam earpiece of claim 14, wherein polymer mixture has an isocyanate index in the range of between 92 and 104.

17. The foam earpiece of claim 14, wherein the polymer mixture includes a filler material having a particle size of about 5 microns to about 100 microns.

18. The foam earpiece of claim 17, wherein the filler material is included in the polymer mixture in a volume fraction of between 0.075 to 0.225.

19. The foam earpiece of claim 17, wherein the polyurethane foam material is crushed to rupture cellular walls of the polyurethane foam material to create at least a portion of the pores between adjacent open cells.

20. The foam earpiece of claim 19, wherein the polyurethane foam material is controllably crushed to a thickness of between 30% and 60% of an original thickness of the polyurethane foam material.

21. The foam earpiece of claim 19, wherein the filler material modifies the cellular walls to control the size of the pores when the polyurethane foam material is crushed.

22. The foam earpiece of claim 14, wherein the polyurethane foam material includes a plurality of filler particles embedded in the cellular walls, at least a majority of the filler particles having a channel extending continuously through the filler particle which extends between adjacent open cells of the polyurethane foam material.

23. The foam earpiece of claim 22, wherein the channels of the filler particles form the pores between adjacent open cells.

24. The foam earpiece of claim 14, wherein the polymer mixture includes about 44-46 weight percent of the diisocyanate mixture, about 48-52 weight percent of the polyol mixture and about 3-4 weight percent of the catalyst mixture.

25. The foam earpiece of claim 14 in combination with a sound control device.

26. A method of forming an earpiece member for placement in close proximity to an ear canal of a user for attenuating sound, the method comprising:
   reacting a diisocyanate with a polyol mixture in the presence of a catalyst mixture to form a polyurethane foam material having a plurality of cells defined by interconnected cellular walls;
   crushing the polyurethane foam material to rupture the cellular walls between adjacent cells of the polyurethane foam material, wherein subsequent to crushing the polyurethane foam material, the polyurethane foam material is a non-reticulated foam material having 80% or more open cells interconnected with adjacent open cells by pores extending through the cellular walls between adjacent open cells;
   wherein the average volume of the cells of the polyurethane foam material is between about 8,000 microns$^3$ to about 8,000,000 microns$^3$;
   wherein the average diameter of the pores of the polyurethane foam material is between about 5 microns to about 50 microns; and
   wherein a ratio between the average diameter of the pores to an average diameter of the cells is between 0.02 to 0.75; and
   forming an earpiece member from the polyurethane foam material.

27. The method of claim 26, wherein the polyurethane foam material includes a plurality of filler particles, wherein the plurality of filler particles strengthen the cellular walls of the polyurethane foam material during the crushing step to limit the diameter of the pores of the polyurethane foam material.

28. The method of claim 27, wherein during the crushing step the polyurethane foam material is compressed to a thickness in a range of 30% to 60% of an initial thickness of the polyurethane foam material.

29. The method of claim 26, further comprising:
   dispersing filler particles in the polyurethane foam material.

30. The sound control device of claim 29, further comprising:
   coating a coupling agent onto the filler particles prior to adding the filler particles to the reaction mixture for forming the polyurethane foam material.

31. A sound control device including an earpiece member for placement in close proximity to an ear canal of a user for attenuating sound, the earpiece member comprising:
   a non-reticulated polymeric foam material having a plurality of cells defined by interconnected cellular walls of the polymeric foam material and a plurality of pores extending through the cellular walls between adjacent cells to interconnect adjacent cells of the polymeric foam material;
   wherein the mode volume of the cells of the polymeric foam material is between about 8,000 microns$^3$ to about 8,000,000 microns$^3$;

wherein the mode diameter of the pores of the polymeric foam material is between about 5 microns to about 50 microns; and wherein a ratio between the mode diameter of the pores to a mode diameter of the cells is between 0.02 to 0.75.

32. The sound control device of claim 31, wherein the cells of the polymeric foam material have a mode diameter between about 25 microns to about 250 microns, and wherein a ratio between the mode diameter of the pores to the mode diameter of the cells is between 0.02 to 0.2.

33. A sound control device including an earpiece member for placement in close proximity to an ear canal of a user for attenuating sound, the earpiece member comprising:

a non-reticulated polymeric foam material having a plurality of cells defined by interconnected cellular walls of the polymeric foam material and a plurality of pores extending through the cellular walls between adjacent cells to interconnect adjacent cells of the polymeric foam material;

wherein the polymeric foam material is sufficiently flexible to conform to a contoured portion of a user's anatomy;

wherein the average diameter of the pores of the polymeric foam material is between about 5 microns to about 50 microns; and wherein a ratio between the average diameter of the pores to an average diameter of the cells is between 0.02 to 0.75.

34. The sound control device of claim 33, wherein the polymeric foam material has a compressional modulus in the range of about 0.5 psi to about 4.5 psi measured at 37 degrees Celsius and 50% relative humidity.

35. The sound control device of claim 33, wherein the cells of the polymeric foam material have an average diameter between about 25 microns to about 250 microns, and wherein a ratio between the average diameter of the pores to the average diameter of the cells is between 0.02 to 0.2.

* * * * *